United States Patent
Chen et al.

(10) Patent No.: US 12,239,687 B2
(45) Date of Patent: Mar. 4, 2025

(54) SUSTAINED RELEASE FORMULATIONS USING NON-AQUEOUS MEMBRANE EMULSIFICATION

(71) Applicant: Regeneron Pharmaceuticals, Inc., Tarrytown, NY (US)

(72) Inventors: Hunter Chen, New York, NY (US); Yiming Zhao, Great Neck, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 180 days.

(21) Appl. No.: 17/535,267

(22) Filed: Nov. 24, 2021

(65) Prior Publication Data
US 2022/0160828 A1    May 26, 2022

Related U.S. Application Data

(60) Provisional application No. 63/118,264, filed on Nov. 25, 2020.

(51) Int. Cl.
*A61K 38/17* (2006.01)
*A61K 9/16* (2006.01)

(52) U.S. Cl.
CPC .......... *A61K 38/179* (2013.01); *A61K 9/1658* (2013.01); *A61K 9/1694* (2013.01)

(58) Field of Classification Search
CPC .. A61K 38/179; A61K 9/1658; A61K 9/1694; A61K 38/00; A61K 9/5015;
(Continued)

(56) References Cited

U.S. PATENT DOCUMENTS

| 4,210,529 A | 7/1980 | Petersen |
| 4,304,767 A | 12/1981 | Heller et al. |

(Continued)

FOREIGN PATENT DOCUMENTS

| WO | 2017/075072 A1 | 5/2017 | |
| WO | WO-2017106716 A1 * | 6/2017 | ........... A61K 38/177 |

(Continued)

OTHER PUBLICATIONS

Byjus, Ester structure uses, obtained online at https://byjus.com/chemistry/ester/, downloaded on May 30, 2023. (Year: 2023).*

(Continued)

*Primary Examiner* — Isaac Shomer
*Assistant Examiner* — Bryan James Rego
(74) *Attorney, Agent, or Firm* — McCarter & English, LLP; John P. Isacson; Alexa Marie J. Derkasch

(57) ABSTRACT

Non-aqueous membrane emulsion methods for producing polymeric and polymer-coated microparticles are provided. Some embodiments provide methods for producing a sustained release or controlled release microparticle by combining micronized protein powder and a polymer into a hydrocarbon solvent to form a non-aqueous first solution, agitating the first non-aqueous solution to form a suspension, feeding the suspension into a dispersion pump, wherein the suspension is infused through a porous membrane into a continuous phase comprising a fluorocarbon liquid and a fluorosurfactant to form a hydrocarbon-in-fluorocarbon emulsion. The hydrocarbon solvent, the fluorocarbon liquid, and the fluorosurfactant are removed, and the microparticles are collected.

20 Claims, 23 Drawing Sheets

(58) Field of Classification Search
CPC .... A61K 9/5031; A61K 9/5089; A61K 47/06; A61K 47/34; A61K 9/0019; C07K 2319/30; C07K 14/71
USPC ........................................................ 424/418
See application file for complete search history.

(56) References Cited

U.S. PATENT DOCUMENTS

| | | | |
|---|---|---|---|
| 4,764,364 | A | 8/1988 | Heller et al. |
| 5,968,543 | A | 10/1999 | Heller et al. |
| 6,063,910 | A | 5/2000 | Debenedetti et al. |
| 6,927,044 | B2 | 8/2005 | Stahl et al. |
| 7,087,411 | B2 | 8/2006 | Daly et al. |
| 7,279,159 | B2 | 10/2007 | Daly et al. |
| 7,396,664 | B2 | 7/2008 | Daly et al. |
| 7,582,298 | B2 | 9/2009 | Stevens et al. |
| 7,879,984 | B2 | 2/2011 | Martin et al. |
| 7,998,477 | B2 | 8/2011 | Yakovlevsky et al. |
| 8,043,617 | B2 | 10/2011 | Stevens et al. |
| 8,062,640 | B2 | 11/2011 | Sleeman et al. |
| 8,309,088 | B2 | 11/2012 | MacDonald et al. |
| 8,586,713 | B2 | 11/2013 | Davis et al. |
| 8,735,095 | B2 | 5/2014 | Martin et al. |
| 8,871,209 | B2 | 10/2014 | Stitt et al. |
| 8,945,559 | B2 | 2/2015 | Dix et al. |
| 9,018,356 | B2 | 4/2015 | Sleeman et al. |
| 9,079,948 | B2 | 7/2015 | Orengo et al. |
| 9,132,192 | B2 | 9/2015 | Daly et al. |
| 9,173,880 | B2 | 11/2015 | Dix et al. |
| 9,228,014 | B2 | 1/2016 | Classon et al. |
| 9,260,515 | B2 | 2/2016 | Stitt et al. |
| 9,265,827 | B2 | 2/2016 | Wiegand et al. |
| 9,302,015 | B2 | 4/2016 | Papadopoulos et al. |
| 9,353,176 | B2 | 5/2016 | MacDonald et al. |
| 9,402,898 | B2 | 8/2016 | Walsh et al. |
| 9,447,173 | B2 | 9/2016 | Gurnett-Bander et al. |
| 9,453,072 | B2 | 9/2016 | Murphy et al. |
| 9,475,875 | B2 | 10/2016 | Kirshner et al. |
| 9,540,449 | B2 | 1/2017 | Yancopoulos et al. |
| 9,587,029 | B2 | 3/2017 | Okamoto et al. |
| 9,637,535 | B2 | 5/2017 | Murphy et al. |
| 9,657,099 | B2 | 5/2017 | Okamoto et al. |
| 9,657,102 | B2 | 5/2017 | Smith et al. |
| 9,718,872 | B2 | 8/2017 | Kyratsous et al. |
| 9,771,414 | B2 | 9/2017 | Kyratsous et al. |
| 9,795,121 | B2 | 10/2017 | Hu et al. |
| 9,938,345 | B2 | 4/2018 | Papadopoulos et al. |
| 9,987,500 | B2 | 6/2018 | Papadopoulos et al. |
| 10,125,188 | B2 | 11/2018 | Gurnett-Bander et al. |
| 11,135,586 | B2 * | 10/2021 | Tang ................. B01L 3/502769 |
| 2014/0271681 | A1 | 9/2014 | Martin et al. |
| 2015/0266966 | A1 | 9/2015 | Smith et al. |
| 2016/0017029 | A1 | 1/2016 | Walsh et al. |
| 2016/0114325 | A1 * | 4/2016 | Tang ................. B01L 3/502761 436/180 |
| 2019/0031741 | A1 | 1/2019 | Gurnett-Bander et al. |
| 2022/0008505 | A1 * | 1/2022 | Zhao ..................... A61K 9/0019 |
| 2022/0257707 | A1 * | 8/2022 | Zhao ..................... A61K 9/1641 |

FOREIGN PATENT DOCUMENTS

| | | | | |
|---|---|---|---|---|
| WO | 2017/186073 A1 | 11/2017 | | |
| WO | WO-2019077114 A1 * | 4/2019 | ......... | B01F 17/0057 |
| WO | 2021/108548 A1 | 6/2021 | | |

OTHER PUBLICATIONS

Mana, Zohra, Yann Pellequer, and Alf Lamprecht. "Oil-in-oil microencapsulation technique with an external perfluorohexane phase." International journal of pharmaceutics 338.1-2 (2007): 231-237. (Year: 2007).*

Mana, Zohra et al. "Oil-in-oil microencapsulation technique with an external perfluorohexane phase." International journal of pharmaceutics vol. 338,1-2 (2007): 231-7. doi:10.1016/j.ijpharm.2007.02.010 (Year: 2007).*

Vladisavljević, Goran T, and Richard A Williams. "Recent developments in manufacturing emulsions and particulate products using membranes." Advances in colloid and interface science vol. 113,1 (2005): 1-20. doi:10.1016/j.cis.2004.10.002 (Year: 2005).*

Homaeigohar, S. Sh, K. Buhr, and K. Ebert. "Polyethersulfone electrospun nanofibrous composite membrane for liquid filtration." Journal of Membrane Science 365.1-2 (2010): 68-77.) (Year: 2010).*

Ashkenazi et al., Protection against endotoxic shock by a tumor necrosis factor receptor immunoadhesin. Proc Natl Acad Sci U S A. Dec. 1, 1991;88(23):10535-9.

Astete et al., Synthesis and characterization of PLGA nanoparticles. J Biomater Sci Polym Ed. 2006; 17(3):247-89.

Bustami et al., Generation of micro-particles of proteins for aerosol delivery using high pressure modified carbon dioxide. Pharm Res. Nov. 2000;17(11):1360-6.

Byrn et al., Biological properties of a CD4 immunoadhesin. Nature. Apr. 12, 1990;344(6267):667-70.

Heller et al., Poly(ortho esters)—from concept to reality. Biomacromolecules. Sep.-Oct. 2004;5(5):1625-32.

Heller, Ocular delivery using poly(ortho esters), Adv Drug Deliv Rev. Dec. 13, 2005;57(14):2053-62.

Hollenbaugh et al., Construction of immunoglobulin fusion proteins. Curr Protoc Immunol. May 2002;Chapter 10:Unit 10.19A.

Juang, Receptor-Fc fusion therapeutics, traps, and Mimetibody technology. Curr Opin Biotechnol. Dec. 2009;20(6):692-9.

Labet et al., Synthesis of polycaprolactone: a review. Chem Soc Rev. Dec. 2009;38(12):3484-504.

Martinac et al., Spray-dried chitosan/ethylcellulose microspheres for nasal drug delivery: swelling study and evaluation of in vitro drug release properties. J Microencapsul. Aug. 2005;22(5):549-61.

Raghuvanshi et al., Stabilization of dichloromethane-induced protein denaturation during microencapsulation. Pharm Dev Technol. May 1998;3(2):269-76.

Sinha et al., Poly-epsilon-caprolactone microspheres and nanospheres: an overview. Int J Pharm. Jun. 18, 2004;278(1):1-23.

Vladisavljevic et al., Recent developments in manufacturing emulsions and particulate products using membranes. Adv Colloid Interface Sci. Mar. 17, 2005;113(1):1-20.

Han et al., Insulin nanoparticle preparation and encapsulation into poly(lactic-co-glycolic acid) microspheres by using an anhydrous system. Int J Pharm. Aug. 13, 2009;378(1-2):159-66.

Holt et al., Synthesis of novel fluorous surfactants for microdroplet stabilisation in fluorous oil streams. Journal of Fluorine Chemistry. Mar. 2010; 131(3):398-407.

International Search Report and Written Opinion for Application No. PCT/US2021/060800, dated Mar. 18, 2022, 15 pages.

* cited by examiner

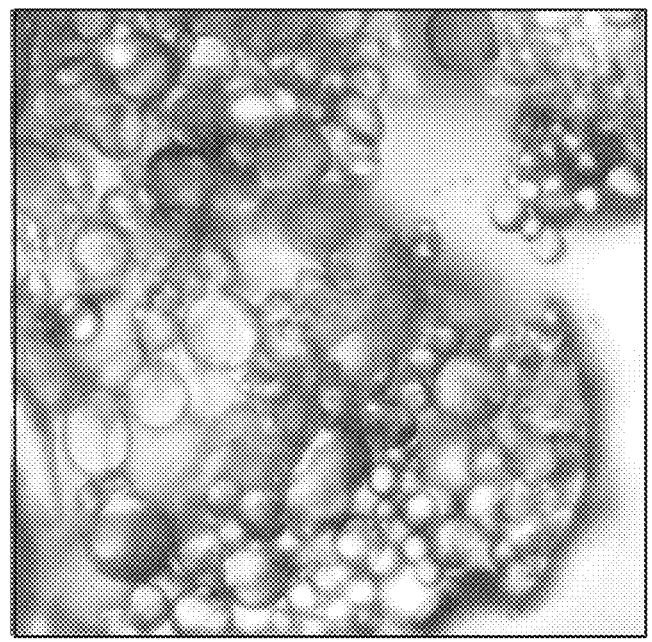
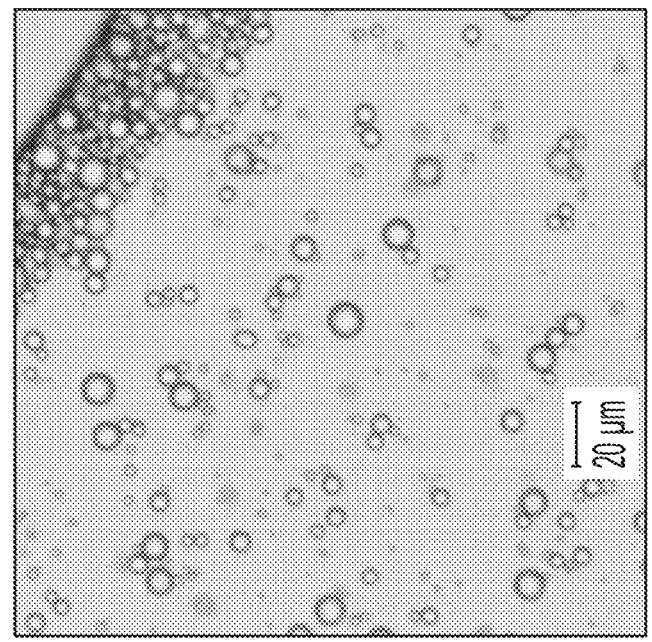
FIG. 2B
FIG. 2A

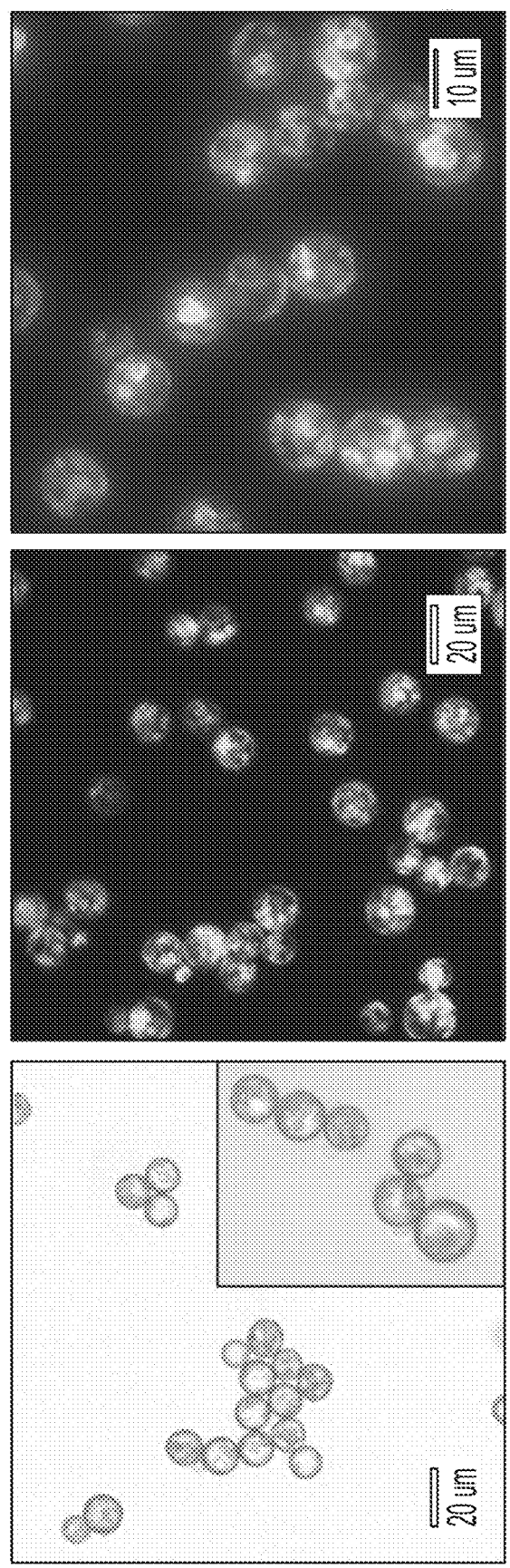

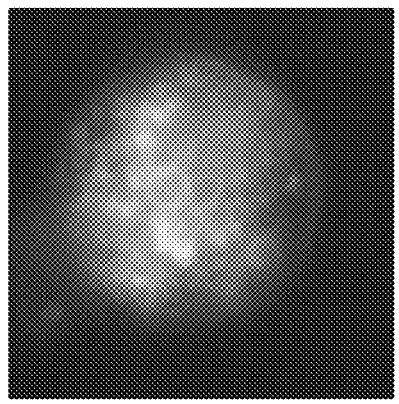
FIG. 8C
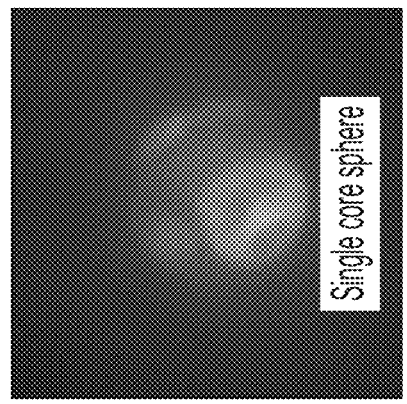
Single core sphere
FIG. 8D
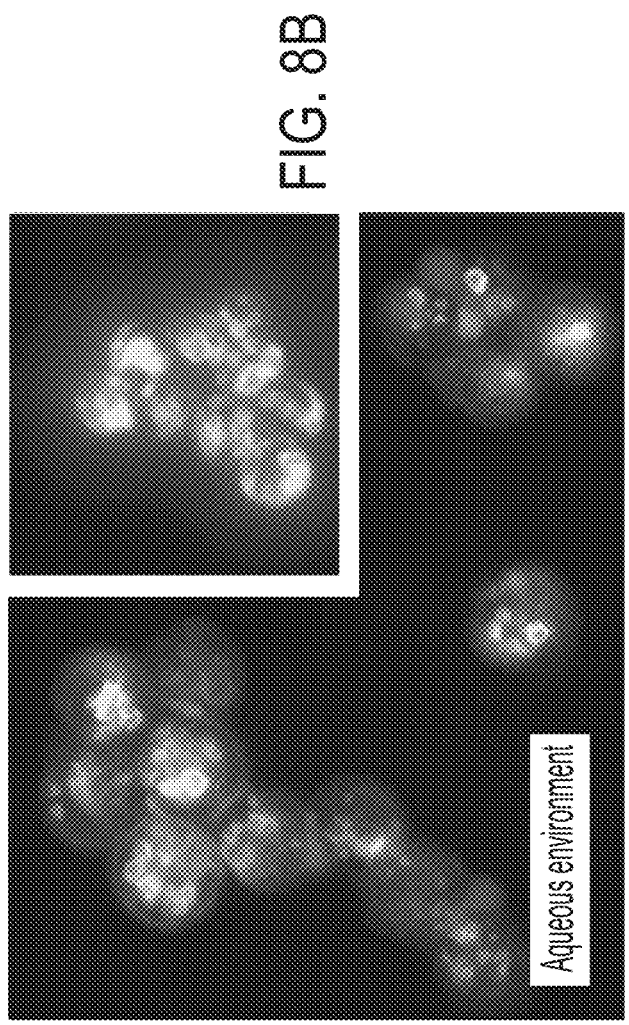
FIG. 8B
Aqueous environment
FIG. 8A

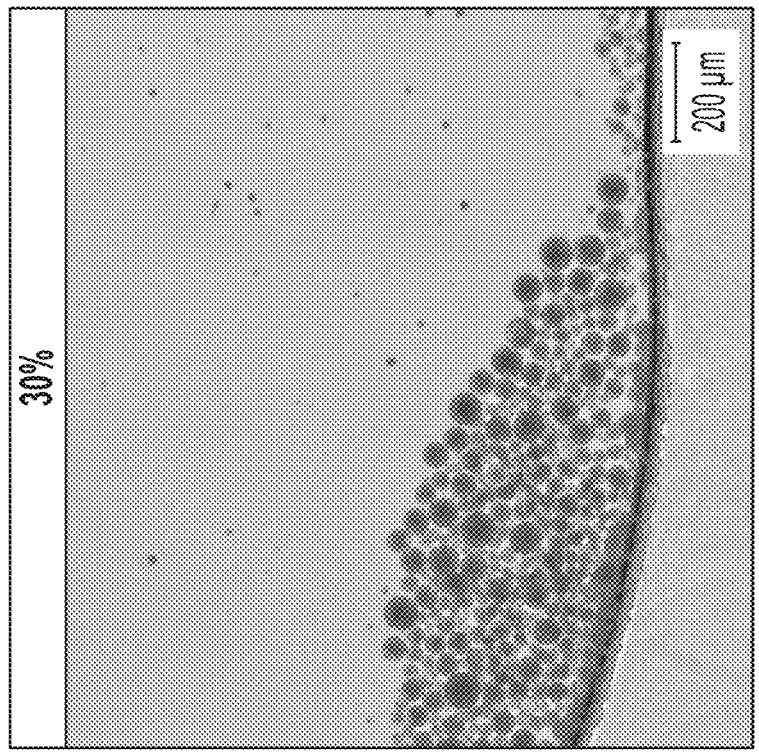
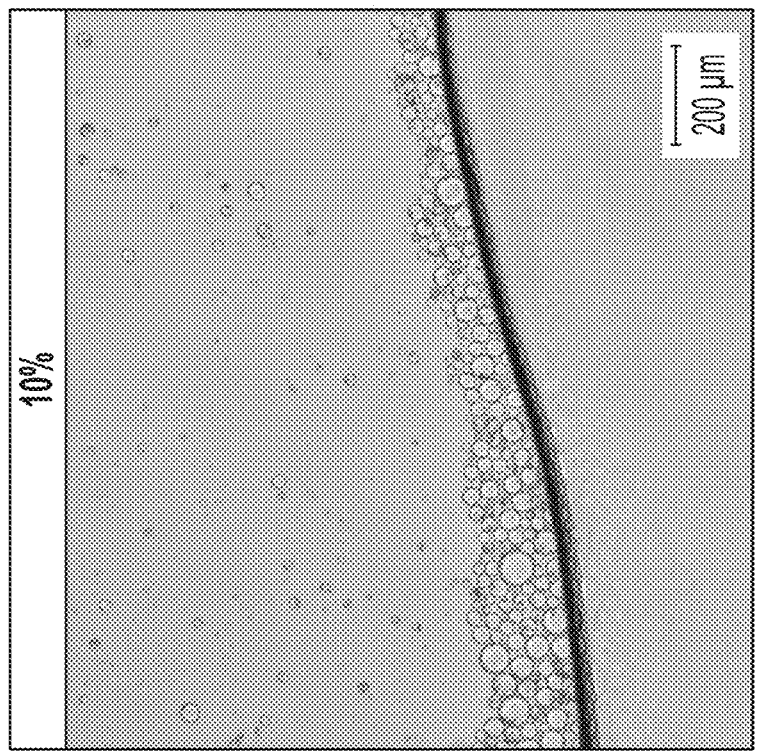
FIG. 10B
FIG. 10A

VEGF-TRAP SDP Encapsulated in Polylactide (PLA)

scale bar: left, middle: 20 um / right: 50 um

SUSTAINED RELEASE FORMULATIONS USING NON-AQUEOUS MEMBRANE EMULSIFICATION

This application claims priority to U.S. Application Ser. No. 63/118,264, filed Nov. 25, 2020, which is hereby incorporated by reference.

TECHNICAL FIELD OF THE INVENTION

Aspects of the invention are generally related to drug microsphere formulations and methods of making them using non-aqueous emulsion systems generated by membrane emulsification method.

BACKGROUND OF THE INVENTION

The extended release delivery of a therapeutic protein toward a biologically relevant target is desirable for the treatment of medical conditions, such as cancer, cardiovascular disease, vascular conditions, orthopedic disorders, dental disorders, wounds, autoimmune disease, gastrointestinal disorders, and ocular diseases. Biocompatible and biodegradable polymers and other implantable delivery devices for the controlled and extended delivery of drugs have been in use for decades. For example, in some polymer-based delivery devices, as the polymer degrades over time, the therapeutic drug is slowly released.

Extended release can be desirable for patient compliance. In particular, reducing the number of injections can be beneficial, especially where a doctor is required to do the injection, such as in the case of intraocular therapeutics. There is an unmet medical need for extended release formulations to deliver drugs effectively over time with as few injections as possible. In the case of other diseases, for example cancer and diseases of inflammation, there is a need for improved implantable extended release formulations containing stable and effective protein therapeutics.

Therapeutic macromolecules, such as antibodies, receptor Fc-fusion proteins, trap proteins and mini-trap proteins must be formulated in a manner that not only makes the molecules suitable for administration to patients, but also maintains their stability during storage and while at the site of administration. For example, therapeutic proteins (e.g., antibodies and fusion proteins) in aqueous solution are prone to degradation, aggregation and/or undesired chemical modifications unless the solution is formulated properly. The stability of a protein therapeutic in liquid formulation depends not only on the kinds of excipients used in the formulation, and the amounts and proportions of those excipients relative to one another, but also on the concentration of the soluble protein. Considerations aside from stability must also be taken into account when preparing a therapeutic protein formulation. Examples of such additional considerations include the viscosity of the solution and the concentration of therapeutic protein that can be accommodated by a given formulation. When formulating a therapeutic protein for extended release, great care must be taken to arrive at a formulation that remains stable over time and at storage and physiological temperature, contains an adequate concentration of antibody, and possesses other properties which enable the formulation to be conveniently administered to patients.

Some extended release formulations are produced using a variety of encapsulation methodologies including: internal phase separation, interfacial polymerization, formation of multiple emulsions, Layer-by-Layer adsorption of polyelectrolytes and soft templating techniques. Water-in-oil-in-water (W/O/W) multiple emulsions is the most common type of multiple emulsions and enables the encapsulation of aqueous/hydrophilic cores directly in aqueous suspension. Unfortunately, aqueous emulsion systems have specific problems when used to encapsulate biological active agents into extended release formulations. For example, precipitation of the proteins occurs at the aqueous organic interface with concomitant reduction in their immunoreactivity (Raghuvanshi, R., et al., *Pharm Dev Technol*, 3(2):269-76 (1998)). In some aqueous emulsion systems, water can diffuse into the organic phase and hydrolyze the protein. After hydrolysis, protein droplets start to merge and escape into the aqueous environment and aggregate or precipitate. After hardening, voids and water channels appear in the microparticle where protein once was but escaped into the aqueous environment.

Non-aqueous emulsions could replace regular aqueous emulsions wherever the presence of water is undesirable. However, there are few reports in the literature or prior art regarding non-aqueous emulsions. Two types of hydrocarbon-based non-aqueous emulsion system are known: (1) two immiscible organic solvents, stabilized by blocking copolymers (e.g., hexane/dimethylformamide); and (2) Oil-immiscible polar solvents (e.g., formamide, acetonitrile) replacing water using existing surfactants. Previously, water-in-perfluorinated oil (W/F) emulsions has been investigated and applied widely in droplet-based microfluidics for single-cell or single-molecule biological assays. In these studies, PFPE-PEG-PFPE has been used as a fluorosurfactant (FS) for stabilizing water droplets in fluorocarbon solvents.

Although many immiscible-solvent-pairs are available, normally one polar and one non-polar, the challenge is to find a pair that is suitable for synthesis of polymer microspheres. Typical biodegradable polymers, e.g. Poly (lactide-co-glycolide) (PLGA), Polylactic acid (PLA), Poly(ortho ester) (POE) are mostly soluble in solvents with medium polarity such as chloroform, dichloromethane, ethyl acetate, etc. This limits the selection of continuous phase. In addition, compatibility with process, toxicity, safety, and residual solvents are concerns of using those organic solvents and need to be considered for use as a pharmaceutical product.

Fluorocarbons can be used as the continuous phase in a non-aqueous emulsion system because of the following general properties:

1. Fluorocarbons are neither "hydrophobic" nor "hydrophilic", they are immiscible with most organic (hydrocarbon) solvents which made them ideal as the continuous phase for hydrocarbon droplet emulsions.
2. Fluorocarbons are non-solvents for proteins and other hydrophilic molecules, hydrocarbon-based polymers, and organic excipients, i.e. these types of molecules will not be soluble in fluorocarbon.
3. Fluorocarbons have low viscosities.
4. Fluorocarbons are chemically inert and can be relatively less toxic or corrosive compared to commonly used hydrocarbon solvents.
5. Fluorocarbons are volatile and recyclable.

Previous literature reported various kinds of emulsion systems containing fluorocarbon have been fabricated through microfluidics methods, such as water-in-fluorocarbon (W/F), water-in-fluorocarbon-in-water (W/F/W) double emulsion, water/fluorocarbon/oil/water (W/F/O/W) triple emulsion, fluorocarbon/hydrocarbon/water (F/H/W) double emulsion, and hydrocarbon/fluorocarbon/water (H/F/W) double emulsion. Some of these emulsions have been used for synthesis of polymeric microspheres. However, all of them are still aqueous-based emulsion systems using water as dispersed or continuous phase.

Regardless of the type of emulsion used, microsphere or microparticle size distribution is typically wide, and the size cannot be easily controlled to meet the target without extensive process optimization and control strategies. Thus, there remains a need to develop new methods that control the microsphere or microparticle size to meet the target without extensive process optimization and control strategies.

Therefore, it is an object of the invention to provide non-aqueous membrane emulsion systems and methods for the production of drug formulations and methods of their use.

There is another object of the invention to provide extended release formulations with improved protein stability and stable extended release and controlled size distribution.

SUMMARY OF THE INVENTION

Non-aqueous membrane emulsion methods for producing polymeric and polymer-coated microparticles are provided. Some embodiment provide a method for producing a sustained release or controlled release microparticle by combining micronized protein powder and a polymer into a hydrocarbon solvent to form a non-aqueous first solution, agitating the first non-aqueous solution to form a suspension, feeding the suspension into a dispersion cell, wherein the suspension is infused through a porous membrane into a continuous phase comprising a fluorocarbon liquid and a fluorosurfactant under a tangent flow of the continuous phase to form a hydrocarbon-in-fluorocarbon emulsion (membrane emulsification). The method further includes the steps of adding a hydrofluoroester to the hydrocarbon-in-fluorocarbon emulsion and removing the hydrocarbon solvent from the hydrocarbon phase to provide hardened microparticles. In some embodiments, a mixture of the hydrofluoroester and fluorocarbon is added to the emulsion to aid in the removal of the hydrocarbon. In some embodiments, the method includes subsequently adding additional pure hydrofluoroester to the emulsion. The method further includes removing the fluorocarbon liquid to isolate the microparticles, wherein the microparticles contain protein encapsulated within a matrix of the polymer. The method optionally includes washing the microparticles in the fluorocarbon liquid to remove residual fluorosurfactant, removing the fluorocarbon liquid and harvesting the microparticles for example by vacuum filtration. In some embodiments the vacuum filtration uses a polyethersulfone membrane filter. In some embodiments, the protein powder is produced from an antibody or antigen-binding fragment thereof, a fusion protein, or a recombinant protein. In some embodiments, the protein is a VEGF trap protein, for example aflibercept. In some embodiments, the emulsion is formed by bulk emulsification.

In some embodiments, the hydrocarbon solvent is selected from the group consisting of dichloromethane, chloroform, toluene, ethyl acetate, tetrahydrofuran, or a combination thereof.

In some embodiments, the fluorocarbon solution comprises 1,1,2,2,3,3,4,4,4-nonafluoro-N,N-bis(1,1,2,2,3,3,4,4,4-nonafluorobutyl)butan-1-amine.

In some embodiments, the fluorosurfactant is Perfluoropolyether-b-Polyethylene glycol-b-Perfluoropolyether. Some embodiments have 0.1 to 5.0% w/v fluorosurfactant, typically about 0.5% w/v fluorosurfactant.

In some embodiments, the hydrofluoroester is 2-(trifluoromethyl)-3-ethoxydodecafluorohexane.

In some embodiments, the protein powder to polymer ratio is 0%-30%.

In some embodiments, the porous membrane is a stainless steel membrane, optionally a fluorophilic-coated stainless steel membrane.

The fluorocarbon and hydrocarbon liquids can be removed by evaporating the fluorocarbon and hydrocarbon liquids under ambient atmospheric pressure or under vacuum. In some embodiments, the fluorocarbon liquid contains hydrofluoroether (HFE). In some embodiments HFE is added to the non-aqueous emulsion to rapidly extract the hydrocarbon into the fluorocarbon liquid to accelerate microsphere hardening. In some embodiments, the protein powder is micronized protein powder. In some embodiments, the microparticles are washed to remove any residual hydrocarbon solvent, fluorocarbon liquid, fluorosurfactant, or a combination thereof remaining on the microparticles. An exemplary fluorocarbon liquid includes a perfluoro C5-C18 compound, including but not limited to 1,1,2,2,3,3,4,4,4-nonafluoro-N,N-bis(1,1,2,2,3,3,4,4,4-nonafluorobutyl)butan-1-amine. Exemplary hydrocarbon solvents include, but are not limited to dichloromethane, chloroform, ethyl acetate, and combinations thereof. An exemplary fluorosurfactant is Perfluoropolyether-b-Polyethylene glycol-b-Perfluoropolyether (PFPE-PEG-PFPE) tri-block co-polymer. An exemplary bioerodible polymer is polyorthoester (POE). In some embodiments the protein is an antibody or antigen binding fragment thereof, a fusion protein, or a recombinant protein. In some embodiments, the protein is spray-dried VEGF Trap protein. In some embodiments, the microparticles have a diameter of 1.0 to 100 µm, 1.0 to 200 µm, or 30 to 60 µm. In some embodiments, the microparticles formed by the disclosed non-aqueous emulsion methods are flowable microparticle compositions. The disclosed, flowable microparticle compositions can be suspended in a pharmaceutically acceptable excipient, for example pH buffered saline, or suspended in an oily vehicle such as medium chain triglycerides. The flowable microparticle compositions can be administered parenterally, for example using a syringe with a 27 G needle. In some embodiments the microsphere or microparticle size distribution is less than 10 CV %. In some embodiments the microsphere size distribution is from 10 to 20 CV %.

Another embodiment provides a method of producing a polymer or polymer-coated microparticles by combining 1.0 to 30.0% w/w of total solid spray dried-protein in a hydrocarbon solution to form a non-aqueous first solution, agitating the first non-aqueous solution to form a suspension, feeding the suspension into a dispersion cell, wherein the suspension is infused through a porous membrane into a continuous phase comprising a fluorocarbon liquid and 0.1 to 5.0% w/v fluorosurfactant under a tangent flow of the continuous phase to form a hydrocarbon-in-fluorocarbon emulsion, removing the hydrocarbon solvent to provide hardened polymer or polymer-coated microspheres, and removing the fluorocarbon liquid to isolate the microparticles, wherein the microparticles comprise protein encapsulated within a matrix of polymer. In some embodiments, the feeding of the suspension is at a rate of 0.1 to 1.0 ml/min. In some embodiments, the method further includes the step of adding a hydrofluoroester into the fluorocarbon liquid of the hydrocarbon-in-fluorocarbon emulsion as a co-solvent to extract the hydrocarbon solvent from dispersed phase to the continuous phase and assist in accelerating the hardening of the microparticles.

In some embodiments the microparticles produced by membrane emulsion have little or no pores or channels in the polymer surface or interior matrix of the microparticles.

Still another embodiment provides a pharmaceutical composition containing polymer-coated microparticles produced using the non-aqueous membrane emulsion methods disclosed herein.

In some embodiments the size of the microparticles can be tuned to a desired diameter or size by varying formulation compositions and process parameters.

BRIEF DESCRIPTION OF THE DRAWINGS

FIG. 2A is a micrograph of blank POE microspheres formed via H/F emulsion. FIG. 2B is a micrograph showing POE aggregation found with low FS content.

FIG. 7A is a bright field micrograph of VEGF Trap F-SDP-encapsulated microspheres. FIG. 7B is a fluorescence image of VEGF Trap F-SDP-encapsulated microspheres (bar=20 μm). FIG. 7C is a fluorescence image of VEGF Trap F-SDP-encapsulated microspheres (bar=10 μm). Green fluorescent images are depicted in gray scale in FIGS. 7B and 7C.

FIGS. 8A-8D are fluorescence images of VEGF Trap F-SDP-encapsulated POE microspheres placed in aqueous environment. Note that the F-SDP retained its original size and morphology within the droplet. Green fluorescent images are depicted in gray scale.

FIGS. 10A and 10B are micrographs of microparticles loaded with 10% and 30% w/w VEGF Trap SDP respectively.

DETAILED DESCRIPTION OF THE INVENTION

I. Definitions

Figure 1A:
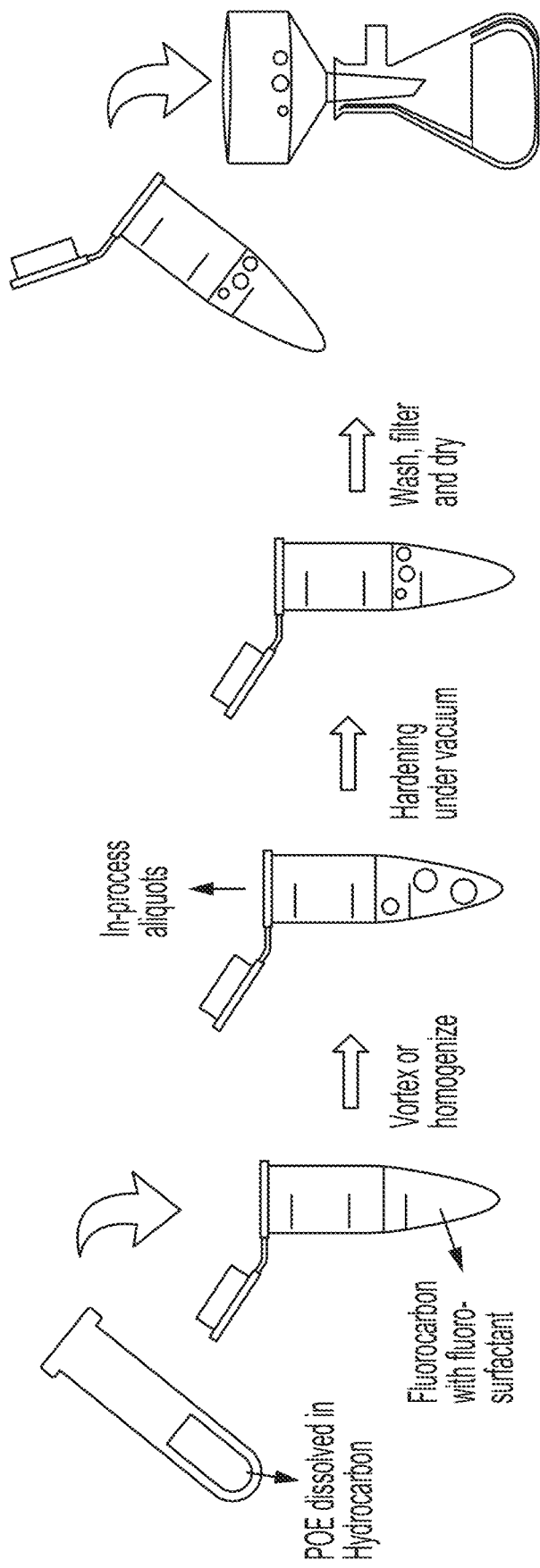
FIG. 1A is a diagram showing the process of blank POE microsphere production via H/F based bulk emulsion—Scheme 1.

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

All numerical limits and ranges set forth herein include all numbers or values thereabout or there between of the numbers of the range or limit. The ranges and limits described herein expressly denominate and set forth all integers, decimals and fractional values defined and encompassed by the range or limit. Thus, a recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

"Blending" provides blending forces, which include compressive shear forces and cavitation. Techniques and methodologies include, but are not limited to, homogenization, vortexing, sonication, stirring, churning, whisking, shaking, emulsifying, agitating, and/or combinations thereof. The application of blending forces can be constant or periodic.

The terms "microsphere" and "microparticle" are used interchangeably.

"Protein" refers to a molecule comprising two or more amino acid residues joined to each other by a peptide bond. Protein includes polypeptides and peptides and may also include modifications such as glycosylation, lipid attachment, sulfation, gamma-carboxylation of glutamic acid residues, alkylation, hydroxylation and ADP-ribosylation. Proteins can be of scientific or commercial interest, including protein-based drugs, and proteins include, among other things, enzymes, ligands, receptors, antibodies and chimeric or fusion proteins. Proteins are produced by various types of recombinant cells using well-known cell culture methods, and are generally introduced into the cell by genetic engineering techniques (e.g., such as a sequence encoding a chimeric protein, or a codon-optimized sequence, an intronless sequence, etc.) where it may reside as an episome or be intergrated into the genome of the cell.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in U.S. Pat. No. 8,586,713, which is incorporated by reference into this application.

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et al., Proc. Natl. Acad. Sci. USA 88: 10535, 1991; Byrn et al., Nature 344:677, 1990; and Hollenbaugh et al., "Construction of Immunoglobulin Fusion Proteins", in Current Protocols in Immunology, Suppl. 4, pages 10.19.1-10.19.11, 1992. "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein comprises two or more distinct receptor chains that bind to a one or more ligand(s). For example, an Fc-fusion protein is a trap, such as for example an IL-1 trap or VEGF trap.

Proteins lacking Fc portions, such as recombinantly produced enzymes and mini-traps, also can be made according to the inventions. Mini-traps are trap proteins that use a multimerizing component (MC) instead of an Fc portion, and are disclosed in U.S. Pat. Nos. 7,279,159 and 7,087,411.

"Micronized protein particle" or "protein particle" means a particle containing multiple molecules of protein with low, very low, or close to zero amounts of water (e.g., <3% water by weight). As used herein, the micronized protein particle is generally spherical in shape and has an ECD ranging from 2 microns to about 35 microns. The micronized protein particle is not limited to any particular protein entity, and is suited to the preparation and delivery of a therapeutic protein. Common therapeutic proteins include inter alia antigen-binding proteins, such as e.g., soluble receptor fragments, antibodies (including IgGs) and derivatives or fragments of antibodies, other Fc containing proteins, including Fc fusion proteins, and receptor-Fc fusion proteins, including the trap-type proteins (Huang, C., Curr. Opin. Biotechnol. 20: 692-99 (2009)) such as e.g. VEGF Trap.

II. Production of Microsphere Formulations Using Hydrocarbon-Fluorocarbon Membrane Emulsions Systems and methods for formulating pharmaceutical compositions using anhydrous or non-aqueous membrane emulsion systems are provided. The disclosed anhydrous membrane emulsion methods overcome several problems with existing aqueous emulsion systems when encapsulating hydrophilic drug molecules. For example, comparative studies between the disclosed anhydrous emulsion systems and existing aqueous emulsion systems provided herein show that formulations produced using aqueous emulsions systems leak drug, for example a protein drug, from emulsion droplets into the aqueous continuous phase during production. This leakage of drug from the emulsion droplets results in low encapsulation efficacy. The disclosed non-aqueous based membrane emulsion methods described herein encapsulate drug molecules, including but not limited to hydrophilic drugs such as proteins, with increased encapsulation efficacy relative to aqueous emulsion systems, retain original protein particulate structure, or a combination thereof. The disclosed anhydrous membrane emulsion systems and methods can produce encapsulated drug formulations by bulk methods (for example, agitation, homogenization, sonication) and other conventional methods. The systems and methods can also be applied to a wide range of polymer materials, solid-state payloads, and emulsification methods. The summary below shows the results of comparison of different emulsion takes demonstrating that the non-aqueous emulsion systems are a significant improvement in microparticle encapsulation compared to aqueous emulsion systems.

Summary of Methods and Results

| Solvent system | Emulsion Method | Dispersed Phase | Continuous Phase | Key results |
|---|---|---|---|---|
| S/O/W | Bulk (agitation or homogenization) | DCM | Water, 1% PVA | Hollow or empty spheres, poor encapsulation |
| S/H/F | Bulk (agitation) | Ethyl Acetate | FC-40, 0.2-2% Pico-surf™ 1 | Microspheres are flowable, resuspendable, and encapsulating protein up to 30% w/w. The micronized protein retained its original particulate size and morphology. Encapsulated protein has retained high purity. Microspheres have smooth surfaces absent of pores or channels. |

A. Solid-in-Hydrocarbon-in-Fluorocarbon (S/H/F) Membrane Emulsions

Membrane emulsification (ME) in general is a relatively new technique for the highly controlled production of particulates that allows good size control and narrow size distribution (G. T. Vladisavljević and R. A. Williams, Adv. Colloid Interface Sci., vol. 113(1): 1-20, (2005)). To date, many different types of membranes have been developed for ME including Shirasu Porous Glass (SPG), cellulose acetate, polymer, anodic porous alumina, and silicon microchannels. For the disclosed ME methods, a stainless steel membrane with laser drilled pores worked well, and the commercially available equipment by Micropore Technologies (Redcar, UK) enabled the laboratory research process and also scaling-up to GMP manufacturing. In other embodiments, the membrane is selected from the group consisting of including Shirasu Porous Glass (SPG), cellulose acetate, polymer, anodic porous alumina, and silicon microchannels. The tightly controlled membrane pore size of the stainless steel membrane allows all the SDP particles below a limit to pass through the membrane. The straight tubular channel with no tortuous paths reduces the tendency of channel blocking by SDP. In some embodiments, the membrane has fluorophilic coating providing good compatibility with the production of hydrocarbon-in-fluorocarbon (H/F) emulsion. In addition, the stainless membranes are robust, easy to clean, and sterilizable. In some embodiments, the diameter of the pores is 3 µm to 300 µm. In some embodiments, the diameter of the pores is 10, 15, 20, 25, 30, 35, 40, 45, or 50 µm.

Some embodiments provide methods for producing a sustained release or controlled release microparticle by combining micronized protein powder and a polymer into a hydrocarbon solvent to form a non-aqueous first solution, agitating the first non-aqueous solution to form a suspension, feeding the suspension into a dispersion pump, wherein the suspension is infused through a porous membrane into a continuous phase comprising a fluorocarbon liquid and a fluorosurfactant to form a hydrocarbon-in-fluorocarbon emulsion. In some embodiments, the feeding of the suspension is at a rate of 0.1 to 1.0 ml/min. The method further includes the steps of adding a hydrofluoroester to the hydrocarbon-in-fluorocarbon emulsion and removing the hydrocarbon solvent to provide hardened microparticles. In some embodiments, a mixture of the hydrofluoroester and fluorocarbon is added to the emulsion. In some embodiments, the method includes adding additional pure hydrofluoroester to the emulsion. The method further includes removing the fluorocarbon liquid to isolate the microparticles, wherein the microparticles contain protein encapsulated within a matrix of the polymer. The method optionally includes washing the microparticles in the fluorocarbon liquid to remove residual fluorosurfactant, removing the fluorocarbon liquid and harvesting the microparticles for example by vacuum filtration. In some embodiments the vacuum filtration uses a polyethersulfone membrane filter. In some embodiments, the protein powder is produced from an antibody or antigen-binding fragment thereof, a fusion protein, or a recombinant protein. In some embodiments, the protein is a VEGF trap protein, for example aflibercept. In some embodiments, the emulsion is formed by bulk emulsion. In some embodiments, the microparticles have less than 15% burst after 24 hrs followed by a linear sustained release of the drug.

In some embodiments, the protein powder to polymer ratio is 0% to 30%.

In some embodiments, the hydrocarbon solvent is selected from the group consisting of dichloromethane, chloroform, toluene, ethyl acetate, tetrahydrofuran, or a combination thereof.

In some embodiments, the fluorocarbon solution comprises 1,1,2,2,3,3,4,4,4-nonafluoro-N,N-bis(1,1,2,2,3,3,4,4,4-nonafluorobutyl)butan-1-amine.

In some embodiments, the fluorosurfactant is Perfluoropolyether-b-Polyethylene glycol-b-Perfluoropolyether.

In some embodiments, the hydrofluoroester is 2-(trifluoromethyl)-3-ethoxydodecafluorohexane.

In some embodiments, the porous membrane is a stainless steel membrane, optionally a fluorophilic-coated stainless steel membrane.

The fluorocarbon and hydrocarbon liquids can be removed by evaporating the fluorocarbon and hydrocarbon liquids under ambient atmospheric pressure or under vacuum. In some embodiments, the fluorocarbon liquid contains hydrofluoroether (HFE). In some embodiments HFE is added to the non-aqueous emulsion to rapidly extract the hydrocarbon into the fluorocarbon liquid to accelerate microsphere hardening. In some embodiments, the protein powder is micronized protein powder. In some embodiments, the microparticles are washed to remove any residual hydrocarbon solvent, fluorocarbon liquid, fluorosurfactant, or a combination thereof remaining on the microparticles. An exemplary fluorocarbon liquid includes a perfluoro C5-C18 compound, including but not limited 1,1,2,2,3,3,4,4,4-nonafluoro-N,N-bis(1,1,2,2,3,3,4,4,4-nonafluorobutyl)butan-1-amine. Exemplary hydrocarbon solvents include, but are not limited to dichloromethane, chloroform, ethylacetate, and combinations thereof. An exemplary fluorosurfactant is Perfluoropolyether-b-Polyethylene glycol-b-Perfluoropolyether (PFPE-PEG-PFPE) tri-block co-polymer. An exemplary bioerodible polymer is polyorthoester (POE). In some embodiments the protein is an antibody or antigen binding fragment thereof, a fusion protein, or a recombinant protein. In some embodiments, the protein is spray-dried VEGF Trap protein. In some embodiments, the microparticles have a diameter of 1.0 to 100 μm, 1.0 to 200 μm, or 30 to 60 μm. In some embodiments, the microparticles formed by the disclosed non-aqueous emulsion methods are flowable microparticle compositions. The disclosed, flowable microparticle compositions can be suspended in a pharmaceutically acceptable excipient, for example pH buffered saline, or suspended in an oily vehicle such as medium chain triglycerides. The flowable microparticle compositions can be administered parenterally, for example using a syringe with a 27 G needle. In some embodiments the microsphere or microparticle size distribution is less than 10 CV %%. In some embodiments the microsphere size distribution is 10-20 CV %.

Another embodiment provides a method of producing a polymer or polymer-coated microparticles by combining 1.0 to 30.0% w/w of total solid spray dried-protein in a hydrocarbon solution to form a non-aqueous first solution, agitating the first non-aqueous solution to form a suspension, feeding the suspension into a dispersion pump, wherein the suspension is infused through a porous membrane into a continuous phase comprising a fluorocarbon liquid and 0.1 to 5.0% w/v fluorosurfactant under a tangent flow of the continuous phase to form a hydrocarbon-in-fluorocarbon emulsion, removing the hydrocarbon solvent to provide hardened polymer or polymer-coated microspheres, and removing the fluorocarbon liquid to isolate the microparticles, wherein the microparticles comprise protein encapsulated within a matrix of polymer. In some embodiments, the method further includes the step of adding a hydrofluoroester into the fluorocarbon liquid of the hydrocarbon-in-fluorocarbon emulsion prior to removing the hydrocarbon solvent to assist in the removal of the hydrocarbon solvent.

In some embodiments the microparticles produced by membrane emulsion have little or no pores or channels in the polymer surface or interior matrix of the microparticles.

Still another embodiment provides a pharmaceutical composition containing polymer-coated microparticles produced using the non-aqueous membrane emulsion methods disclosed herein.

In some embodiments the size of the microparticles can be tuned to a desired diameter or size by varying formulation compositions and process parameters.

The hydrocarbon and protein solution can be formed by applying blending forces, such as compressive shear forces and cavitation. Techniques include, but are not limited to, homogenization, vortexing, sonication, stirring, churning, whisking, shaking, emulsifying, agitating, and/or combinations thereof. The method further includes the step of removing the hydrocarbon solvent and the fluorocarbon liquid while stirring the emulsion. The hydrocarbon and fluorocarbon liquids can be removed by evaporation optionally while under vacuum. In other embodiments, the microparticles can be harvested by filtration. Removing the hydrocarbon and fluorocarbon liquids hardens the microparticles which can then be harvested. In some embodiments, HFE can be added to the fluorocarbon to help extract the hydrocarbon from the dispersed phase into the fluorocarbon continuous phase for a faster hardening process. HFE is miscible with both fluorocarbon and hydrocarbon and thus can act as a co-solvent to enhance the solubility of hydrocarbon in the fluorocarbon phase. The sustained release microparticles produced by the non-aqueous emulsion method contain protein encapsulated within a matrix of the biodegradable or bioerodible polymer. In some embodiments, the microparticles have a single core-shell structure. In other embodiments, the microparticles have multiple cores dispersed within the polymer. In still other embodiments, the population of microparticles include microparticles having a single core-structures encapsulated by a polymer cortex and microparticles having multi-core structures in the polymer cortex. The fluorocarbon liquid can be a perfluoro C5-C18 compound including but not limited to FC-40, and the hydrocarbon solution is selected from the group of ethyl acetate, chloroform, toluene, ethyl acetate, tetrahydrofuran, and dichloromethane or combinations thereof. In some embodiments the fluorosurfactant is Perfluoropolyether-b-Polyethylene glycol-b-Perfluoropolyether commercially available as Pico-Surf™ 1. In some embodiments, the bioerodible polymer is POE. In other embodiments, the polymer is selected from the group consisting of polylactic acid and poly(lactic-co-glycolic acid). Generally, the protein is an antibody or antigen binding fragment thereof, a fusion protein, a recombinant protein, or a fragment or truncated version thereof. Typically, the protein is micronized, for example by spray-drying, electrospray drying, reversible precipitation, spray freezing, microtemplating, or a combination thereof. In some embodiments, the protein is a VEGF Trap protein or a truncated form thereof. Other proteins that can be used in the disclosed methods are described below. Microparticles produced by the disclosed methods have a polymer cortex that is mostly devoid of pores or channels. The polymer cortex is not perforated. In some embodiments, the microparticles have a diameter of 1 to 200 μm.

1. Hydrocarbon Solvents

In some embodiments, the hydrocarbon solvent (also referred to as hydrocarbon liquid) is selected so that polymeric materials e.g., the biodegradable or bioerodible polymers are soluble in the hydrocarbon. In some embodiments, the hydrocarbon solvent is selected from the group consisting of dichloromethane, chloroform, toluene, ethyl acetate, tetrahydrofuran, or a combination thereof. In some embodiments, the hydrocarbon solvent can contain acetonitrile, dimethylformamide, dimethylsulfoxide, acetone, ethanol, methanol, pentane, propanol, hexane, or a combination thereof.

2. Fluoroliquids

An exemplary fluoroliquid is a fluorocarbon liquid including but not limited to Flourinert™ FC-40 (average MW=650 g/mol) 1,1,2,2,3,3,4,4,4-nonafluoro-N,N-bis(1,1,2,2,3,3,4,4,4-nonafluorobutyl)butan-1-amine (FIG. 1B), Fluorinert™ FC-70 (average MW=821 g/mol) or a combination thereof. In some embodiments the fluorocarbon liquid is or contains hydrofluoroether (HFE). An exemplary HFE includes but is not limited to NOVEC™ 7000 (1-methoxyheptafluoropropane), NOVEC™ 7100 (methoxy-nonafluorobutane), NOVEC™ 7200 (ethoxy-nonafluorobutane), NOVEC™ 7500 (2-(Trifluoromethyl)-3-ethoxydodecafluorohexane. In still other embodiments, the fluorocarbon liquid contains FC-40, FC-70, Novec™ 7500, Novec™ 7100, Novec™ 7000, or combinations thereof. In certain embodiments, the second solution contains a fluorosurfactant (FS) in addition to the fluoroliquid. An exemplary FS is Perfluoropolyether-b-Polyethylene glycol-b-Perfluoropolyether (PFPE-PEG-PFPE) tri-block co-polymer which is commercially available as Pico-Surf™ 1. In some embodiments, the fluorocarbon liquid or the second solution contains FC-40, and Pico-Surf™ 1.

In some embodiments the FS is

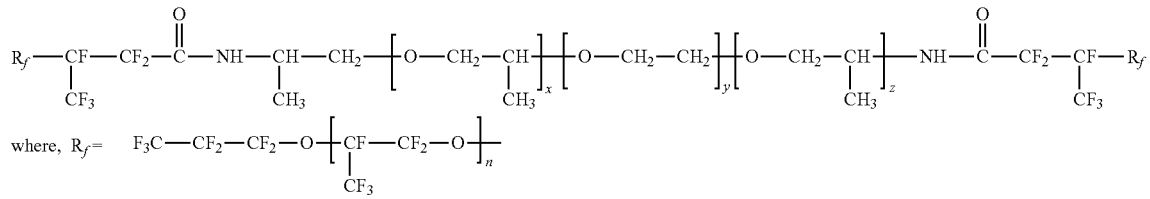

wherein: n~37, x+z~6.0, y~12.5. or wherein n=3.7, x+z~3.6, y~9.0. (Lee, M. et al., *Lab Chip.*, 7:14(3): 509-13 (2014)).

In some embodiments the HFE has the following chemical structure:

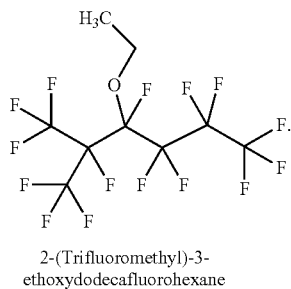 [SMILES: CCOC(F)(C(F)(F)C(F)(F)C(F)(F)F)C(F)(C(F)(F)F)C(F)(F)F]

2-(Trifluoromethyl)-3-ethoxydodecafluorohexane

Other HFEs suitable for use in the process are class of molecules with all of the hydrogen atoms reside on carbons with no fluorine substitution and are separated from the fluorinated carbons by the ether oxygen, i.e. RfORh. HFEs have molecular structures which can be linear, branched, or cyclic, or a combination thereof (such as alkylcycloaliphatic), and are preferably free of ethylenic unsaturation, having a total of about 4 to about 20 carbon atoms. Such HFEs are known and are readily available, either as essentially pure compounds or as mixtures. Due to the lipophilicity and fluorophilicity of HFEs, they are miscible with both fluorocarbon and hydrocarbon. When added to the hydrocarbon/fluorocarbon emulsion they can act as a co-solvent to extract hydrocarbon to the fluorocarbon phase and accelerate the hardening process.

In some embodiments, the hydrocarbon solvent, the fluorocarbon, or both are removed by evaporation optionally under vacuum optionally while the emulsion is stirring. In some embodiments, the microparticles are harvested by filtering, optionally filtering under vacuum.

The percentage of HFE in the fluorocarbon phase can be 0-20% v/v, while increasing the HFE percentage increases the hydrocarbon extraction rate. However, the percentage of HFE cannot be too high as the size and morphology of the microsphere may become harder to control.

3. Erodible or Biodegradable Polymers

In some embodiments, the polymer is a biodegradable or bioerodible polymer. In some embodiments, the polymer is selected from the group consisting of branched or linear polyethylene glycol (PEG), polylactic acid (PLA), polyglycolic acid (PGA), polylactic-polyglycolic copolymer (PLGA), poly-D,L-lactide-co-glycolide (PLGA), PLGA-ethylene oxide fumarate, PLGA-alpha-tocopheryl succinate esterified to polyethylene glycol 1000 (PLGA-TGPS), polyanhydride poly[1,6-bis(p-carboxyphenoxy)hexane] (pCPH), poly(hydroxbutyric acid-cohydroxyvaleric acid) (PHB-PVA), polyethylene glycol-poly (lactic acid) copolymer (PEG-PLA), poly-ε-caprolactone (PCL), poly-alkyl-cyanoacrylate (PAC), poly(ethyl)cyanoacrylate (PEC), poly-isobutyl cyanoacrylate, poly-N-(2-hydroxypropyl)methacrylamide (poly(HPMA)), poly-β-R-hydroxy butyrate (PHB), poly-β-R-hydroxy alkanoate (PHA), poly-β-R-malic acid, phospholipid-cholesterol polymers, 2-dioleoyl-sn-glycero-3-phosphatidylcholine/polyethyleneglycol-distearoylphosphatidylehtanolamine (DOPC/PEG-DSPE)/Cholesterol, polysaccharides, cellulose, ethyl cellulose, methyl cellulose, alginates, dextran and dextran hydrogel polymers, amylose, inulin, pectin and guar gum, chitosan, chitin, heparin, hyaluronic acid, cyclodextrin (CD)-based polyrotaxanes and polypseudorotaxanes, polyaspartates, polyglutamates, polylucine, leucine-glutamate co-polymers, polybutylene succinate, gelatin, collagens, fibrins, fibroin, polyorthoesters, polyorthoester-polyamidine copolymer, polyorthoester-diamine copolymers, polyorthoesters incorporating latent acids, poly(ethylene glycol)/poly(butylene terephthalate) copolymer, and combinations and copolymers thereof. In some embodiments, the polymer is poly-ε-caprolactone (PCL) or a derivative or copolymer thereof. In some embodiments the polymer is PLGA or a derivative or copolymer thereof. In some embodiments, the polymer is ethyl cellulose or a derivative or copolymer thereof. In some embodiments, the polymer is polyorthoester or a derivative or copolymer thereof. In some embodiments, the polymer is polyesteramide.

As used herein, the term "polymer" refers to a macromolecule comprising repeating monomers connected by covalent chemical bonds. Polymers are biocompatible and biodegradable erodible. A biocompatible and biodegradable polymer can be natural or synthetic. Natural polymers include polynucleotides, polypeptides, such as naturally occurring proteins, recombinant proteins, gelatin, collagens, fibrins, fibroin, polyaspartates, polyglutamates, polylysine, leucine-glutamate co-polymers: and polysaccharides, such as cellulose alginates, dextran and dextran hydrogel polymers, amylose, inulin, pectin and guar gum, chitosan, chitin, heparin, and hyaluronic acid. Synthetic biocompatible or biodegradable polymers include polylactic acid (PLA), polyglycolic acid (PGA), polylactic-polyglycolic copolymer (PLGA), poly-D,L-lactide-co-glycolide (PLGA). PLGA-ethylene oxide fumarate. PLGA-alpha-tocopheryl succinate esterified to polyethylene glycol 1000 (PLGA-TGPS), polyanhydride poly[1,6-bis(p-carboxyphenoxy)hexane] (pCPH), poly(hydroxybutyric acid-cohydroxyvaleric acid) (PHB-PVA), polyethylene glycol-poly (lactic acid) copolymer (PEG-PLA), poly-ε-caprolactone (PCL), poly-alkyl-cyanoacrylate (PAC), poly(ethyl)cyanoacrylate (PEC), poly-isobutyl cyanoacrylate, poly-N-(2-hydroxypropyl)methacrylamide (poly(HPMA)), poly-β-R-hydroxy butyrate (PHB), poly-β-R-hydroxy alkanoate (PHA), poly-β-R-malic acid, phospholipid-cholesterol polymers, 2-dioleoyl-snglycero-3-phosphatidylcholine/polyethyleneglycol-distearoylphosphatidylehtanolamine (DOPC/PEG-DSPE)/Cholesterol, ethyl cellulose, cyclodextrin (CD)-based polyrotaxanes and polypseudorotaxanes, polybutylene succinate (PBS), polyorthoesters, polyorthoester-polyamidine copolymers, polyorthoester-diamine copolymers, polyorthoesters incorporating latent acids tom control rates of degradation, and inter alia poly(ethylene glycol)/poly(butylene terephthalate) copolymers.

Ethyl cellulose (EC) is a well-known and readily available biomaterial used in the pharmaceutical and food sciences. It is a cellulose derivative in which some of the glucose hydroxyl groups are replaced with ethyl ether. See Martinac et al., J. Microencapsulation, 22(5): 549-561 (2005) and references therein, which describe methods of using ethyl cellulose as biocompatible polymers in the manufacture of microspheres. See also U.S. Pat. No. 4,210,529 (1980) and references therein for a detailed description of ethyl cellulose and methods of making derivatives of ethyl cellulose.

Poly-D,L-lactide-co-glycolide (PLGA) is also a well-known Food and Drug Administration (FDA) approved biocompatible and biodegradable polymer used in tissue engineering and pharmaceutical delivery systems. PLGA is a polyester comprising glycolic acid and lactic acid monomers. For a description of the synthesis of PLGA and manufacture of PLGA nanoparticles, see Astete and Sabliov, Biomater. Sci. Polym. Ed., 17(3): 247-89 (2006) and references therein.

Poly-ε-caprolactone (PCL) is another biocompatible and biodegradable polymer approved by the FDA for use in humans as a drug delivery device. PCL is a polyester of s-caprolactone, which hydrolyses rapidly in the body to form a non-toxic or low toxicity hydroxycarboxylic acid. For a description of the manufacture of PCL, see Labet and Thielemans, Chemical Society Reviews 38: 3484-3504 (2009) and references therein. For a description of the manufacture and use of PCL-based microspheres and nanospheres as delivery systems, see Sinha et al., Int. J. Pharm., 278(1): 1-23 (2004) and references therein.

Polyorthoester (POE) is a bioerodible polymer designed for drug delivery. It is generally a polymer of a ketene acetal, preferably a cyclic diketene acetal, such as e.g., 3,9-dimethylene-2,4,8,10-tetraoxa spiro[5.5]-undecane, which is polymerized via glycol condensation to form the orthoester linkages. A description of polyorthoester synthesis and various types can be found e.g. in U.S. Pat. No. 4,304,767. Polyorthoesters can be modified to control their drug release profile and degradation rates by swapping in or out various hydrophobic diols and polyols, such as e.g., replacing a hexanetriol with a decanetriol; as well as adding latent acids, such as e.g., glycolide, octanedioic acid or the like, to the backbone to increase pH sensitivity. Custom forms of POE can include glycolic acid in the POE backbone to tune mass loss and drug release. Other modifications to the polyorthoester include the integration of an amine to increase functionality. The formation, description, and use of polyorthoesters are described in U.S. Pat. Nos. 5,968,543; 4,764,364; Heller and Barr, Biomacromolecules, 5(5): 1625-32 (2004); and Heller, Adv. Drug. Deliv. Rev., 57: 2053-62 (2005).

4. Protein Drugs

In some embodiments, the microparticle formulations produced by the disclosed anhydrous emulsion methods and system include a drug. Exemplary drugs include but are not limited to proteins, fusion proteins and fragments thereof, antibodies and antigen binding fragments thereof, and ligand binding domains and proteins. In some embodiments, the protein is VEGF Trap protein (e.g., Aflibercept, which contains the Ig domain 2 of the VEGF receptor Flt1 fused to the Ig domain 3 of the VEGF receptor Flk1 fused to Fc of hIgG1 for example as described in U.S. Pat. Nos. 7,087,411 and 7,279,159, which are herein incorporated by reference in their entirety. In some embodiments, the VEGF Trap protein is a truncated form of VEGF Trap as described in U.S. Pat. No. 7,396,664 which is incorporated by reference in its entirety.

In some embodiments, the protein in the microparticle formulation is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a dual-specific, tetravalent immunoglobulin G-like molecule, termed dual variable domain immunoglobulin (DVD-IG), an IgD antibody, an IgE antibody, an IgM antibody, an IgG antibody, an IgG1 antibody, an IgG2 antibody, an IgG3 antibody, or an IgG4 antibody. In some embodiments, the antibody is an IgG1 antibody. In some embodiments, the antibody is an IgG2 antibody. In some embodiments, the antibody is an IgG4 antibody. In some embodiments, the antibody comprises a chimeric hinge. In still other embodiments, the antibody comprises a chimeric Fc. In some embodiments, the antibody is a chimeric IgG2/IgG4 antibody. In some embodiments, the antibody is a chimeric IgG2/IgG1 antibody. In some embodiments, the antibody is a chimeric IgG2/IgG1/IgG4 antibody.

In some embodiments, the antibody is selected from the group consisting of an anti-Programmed Cell Death 1 antibody (e.g., an anti-PD1 antibody as described in U.S. Pat. No. 9,987,500, an anti-Programmed Cell Death Ligand-1 (e.g., an anti-PD-L1 antibody as described in in U.S. Pat. No. 9,938,345), an anti-D114 antibody, an anti-Angiopoetin-2 antibody (e.g., an anti-ANG2 antibody as described in U.S. Pat. No. 9,402,898), an anti-Angiopoetin-Like 3 antibody (e.g., an anti-AngPtl3 antibody as described in U.S. Pat. No. 9,018,356), an anti-platelet derived growth factor receptor antibody (e.g., an anti-PDGFR antibody as described in U.S. Pat. No. 9,265,827), an anti-Erb3 antibody, an anti-Prolactin Receptor antibody (e.g., anti-PRLR antibody as described in U.S. Pat. No. 9,302,015), an anti-Complement 5 antibody (e.g., an anti-C5 antibody as described in U.S. Pat. No. 9,795,121), an anti-TNF antibody, an anti-epidermal growth factor receptor antibody (e.g., an anti-EGFR antibody as described in U.S. Pat. No. 9,132,192 or an anti-EGFRvIII antibody as described in U.S. Pat. No. 9,475,875), an anti-Proprotein Convertase Subtilisin Kexin-9 antibody (e.g., an anti-PCSK9 antibody as described in U.S. Pat. Nos. 8,062,640 or 9,540,449), an Anti-Growth and Differentiation Factor-8 antibody (e.g. an anti-GDF8 antibody, also known as anti-myostatin antibody, as described in U.S. Pat. Nos. 8,871,209 or 9,260,515), an anti-Glucagon Receptor (e.g. anti-GCGR antibody as described in U.S. Pat. Nos. 9,587,029 or 9,657,099), an anti-VEGF antibody, an anti-IL1R antibody, an interleukin 4 receptor antibody (e.g., an anti-HL4R antibody as described in U.S. Pat. Appln. Pub. No. US2014/0271681A1, U.S. Pat. Nos. 8,735,095 or 8,945,559), an anti-interleukin 6 receptor antibody (e.g., an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (e.g., anti-IL33 antibody as described in U.S. Pat. Nos. 9,453,072 or 9,637,535), an anti-Respiratory syncytial virus antibody (e.g., anti-RSV antibody as described in U.S. Pat. Nos.

9,447,173 and 10,125,188, and U.S. Pat. Appl. Pub. No. US2019/0031741 A1), an anti-Cluster of differentiation 3 (e.g., an anti-CD3 antibody, as described in U.S. Pat. No. 9,657,102), an anti-Cluster of differentiation 20 (e.g., an anti-CD20 antibody as described in U.S. Pat. No. 9,657,102 and US20150266966A1, and in U.S. Pat. No. 7,879,984), an anti-CD19 antibody, an anti-CD28 antibody, an anti-Cluster of Differentiation-48 (e.g., anti-CD48 antibody as described in U.S. Pat. No. 9,228,014), an anti-Fe1 d1 antibody (e.g., as described in U.S. Pat. No. 9,079,948), an anti-Middle East Respiratory Syndrome virus (e.g. an anti-MERS antibody as described in U.S. Pat. No. 9,718,872), an anti-Ebola virus antibody (e.g., as described in U.S. Pat. No. 9,771,414), an anti-Zika virus antibody, an anti-Lymphocyte Activation Gene 3 antibody (e.g., an anti-LAG3 antibody, or an anti-CD223 antibody), an anti-Nerve Growth Factor antibody (e.g., an anti-NGF antibody as described in U.S. Pat. Appln. Pub. No. US2016/0017029 (abandoned) and U.S. Pat. Nos. 8,309,088 and 9,353,176) and an anti-Protein Y antibody. In some embodiments, the bispecific antibody is selected from the group consisting of an anti-CD3× anti-CD20 bispecific antibody (as described in U.S. Pat. No. 9,657,102 and US20150266966A1), an anti-CD3× anti-Mucin 16 bispecific antibody (e.g., an anti-CD3× anti-Muc16 bispecific antibody), and an anti-CD3× anti-Prostate-specific membrane antigen bispecific antibody (e.g., an anti-CD3× anti-PSMA bispecific antibody). In some embodiments, the protein of interest is selected from the group consisting of abciximab, adalimumab, adalimumab-atto, ado-trastuzumab, alemtuzumab, alirocumab, atezolizumab, avelumab, basiliximab, belimumab, benralizumab, bevacizumab, bezlotoxumab, blinatumomab, brentuximab vedotin, brodalumab, brolucizumab, canakinumab, capromab pendetide, certolizumab pegol, cemiplimab, cetuximab, denosumab, dinutuximab, dupilumab, durvalumab, eculizumab, elotuzumab, emicizumab-kxwh, emtansinealirocumab, evinacumab, evolocumab, fasinumab, golimumab, guselkumab, ibritumomab tiuxetan, idarucizumab, infliximab, infliximab-abda, infliximab-dyyb, ipilimumab, ixekizumab, mepolizumab, necitumumab, nesvacumab, nivolumab, obiltoxaximab, obinutuzumab, ocrelizumab, ofatumumab, olaratumab, omalizumab, panitumumab, pembrolizumab, pertuzumab, ramucirumab, ranibizumab, raxibacumab, reslizumab, rinucumab, rituximab, sarilumab, secukinumab, siltuximab, tocilizumab, tocilizumab, trastuzumab, trevogrumab, ustekinumab, and vedolizumab.

In some embodiments, the protein in the complexes is a recombinant protein that contains an Fc moiety and another domain, (e.g., an Fc-fusion protein). In some embodiments, an Fc-fusion protein is a receptor Fc-fusion protein, which contains one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a TRAP protein, such as for example an IL-1 trap (e.g., rilonacept, which contains the IL-1RAcP ligand binding region fused to the Il-1R1 extracellular region fused to Fc of hIgG1; see U.S. Pat. No. 6,927,044, which is herein incorporated by reference in its entirety), or a VEGF trap (e.g., aflibercept or ziv-aflibercept, which comprises the Ig domain 2 of the VEGF receptor Ft1 fused to the Ig domain 3 of the VEGF receptor Flk1 fused to Fc of hIgG10). In other embodiments, an Fc-fusion protein is a ScFv-Fc-fusion protein, which contains one or more of one or more antigen-binding domain(s), such as a variable heavy chain fragment and a variable light chain fragment, of an antibody coupled to an Fc moiety.

In some embodiments, proteins lacking Fc portions, such as recombinantly produced enzymes and mini-traps, also can be made according to the inventions Mini-traps are trap proteins that use a multimerizing component (MC) instead of an Fc portion, and are disclosed in U.S. Pat. Nos. 7,279,159 and 7,087,411.

In some embodiments, the initial protein is in the form of a dry powder, for example a micronized, dry powder. In some embodiments, the protein is spray dried powder (SDP). The use of spray dried protein instead of a solution of protein has the advantages of higher protein loading in the microparticles and better protein stability during the encapsulation process. In some embodiments, the dry protein molecules remain in solid state and surrounded by stabilizers during the whole encapsulation process and storage conditions. In some embodiments, the encapsulated spray dried protein exhibits high recovery and low aggregates, possibly due to minimized surface interaction as only a small portion of surface proteins are exposed to the interface. In some embodiments, the protein is micronized prior to encapsulation.

B. Microparticles

Some embodiments provide a pharmaceutical composition produced using the disclosed non-aqueous membrane emulsion system. In some embodiments, the pharmaceutical composition contains microparticles that have a polymer cortex and micronized protein core. In some embodiments, the microparticles are roughly spherical in shape. Some microparticles and protein cores will approach sphericity, while others will be more irregular in shape. Thus, as used herein, the term "diameter" means each and any of the following: (a) the diameter of a sphere which circumscribes the microparticle or protein core, (b) the diameter of the largest sphere that fits within the confines of the microparticle or the protein core. (c) any measure between the circumscribed sphere of (a) and the confined sphere of (b), including the mean between the two, (d) the length of the longest axis of the microparticle or protein core, (e) the length of the shortest axis of the microparticle or protein core, (f) any measure between the length of the long axis (d) and the length of the short axis (e), including the mean between the two, and/or (g) equivalent circular diameter ("ECD"), as determined by micro-flow imaging (MFI), nanoparticle tracking analysis (NTA), or as volume or number averaged diameter by light scattering methods such as static light scattering (SLS), dynamic light scattering (DLS), or laser diffraction analysis. Diameter is generally expressed in micrometers (μm or micron). Diameter can be determined by optical measurement or scanning electron microscopy measurement.

Microparticles produced by the disclosed non-aqueous emulsion methods multiple molecules of protein with low, very low, or close to zero amounts of water (e.g., < or =3% water by weight). As used herein, the micronized protein particle and has an ECD ranging from 2 microns to about 35 microns, or from 2.0 to 50 μm, or 5.0 to 15.0 μm, 30 to 60 μm, or about 10 μm. The micronized protein particle is not limited to any particular protein entity, and is suited to the preparation and delivery of a therapeutic protein including the proteins described above.

For example, the protein particle may be micronized by spray-drying, lyophilization and milling, jet milling, reversible precipitation in non-solvent, granulation, gradual precipitation (U.S. Pat. No. 7,998,477 (2011)), supercritical fluid precipitation (U.S. Pat. No. 6,063,910 (2000)), or high-pressure carbon dioxide induced particle formation (Bustami et al., Pharma. Res. 17: 1360-66 (2000)). As used herein, the phrase "spray-dry" means a method of producing a dry powder comprising micron-sized particles from a slurry or suspension by using a spray-dryer. Spray dryers employ an atomizer or spray nozzle to disperse the suspension or slurry into a controlled drop size spray. Drop sizes from 10 to 500 μm can be generated by spray-drying. As the solvent (water or organic solvent) dries, the protein substance dries into a micron-sized particle, forming a powder-like substance; or in the case of a protein-polymer suspension, during drying, the polymer hardened shell around the protein load.

In some embodiments the micronized protein is a VEGF Trap protein. Pharmaceutical formulations for the formation of micronized VEGF Trap protein particles may contain from about 10 mg/mL to about 100 mg/mL VEGF Trap protein, about 1.0 to about 50 mg/mL protein, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL VEGF Trap protein.

In some embodiments, the microparticles produced using the disclosed non-aqueous membrane emulsion systems contain a protein particle core within a polymer cortex, have a range of diameters of from about 2 μm to about 70 μm, about 5 μm to about 65 μm, about 10 μm to about 60 μm, about 15 μm to about 55 μm, about 10 μm to about 50 μm, about 1.0 to 15 μm, about 20 μm, about 25 μm, or about 30 μm The size variation in large part reflects the thickness of the polymer cortex, although the diameter of the protein core could contribute to size variation to some extent.

In some embodiments, the microparticles formed by the disclosed non-aqueous emulsion methods are flowable microparticle compositions. The disclosed, flowable microparticle compositions can be suspended in a pharmaceutically acceptable excipient, for example pH buffered saline. The flowable microparticle compositions can be administered parenterally, for example using a syringe such as a syringe with a 27 G needle.

In some embodiments, the microparticles are useful in the time-release or extended release of protein therapeutics. In some embodiments, the microsphere formulations are injected intravitreally, suprachoroidally, or subcutaneously. For example, it is envisioned that the VEGF Trap microparticles are useful in the extended release of VEGF Trap therapeutic protein in, for example, the vitreous or suprachoroidal space for the treatment of vascular eye disorders, or subcutaneous implantation for the extended release of VEGF Trap to treat other disorders.

The microparticles of the instant invention release protein in a physiological aqueous environment at about 37° C. at a relatively constant rate over an extended period of time, to at least 60, 90, 120, or 150 days. In some embodiments, the microparticles have less than 15% burst after 24 hrs followed by a linear sustained release of the drug.

Some embodiments provide a composition of microspheres produced using the non-aqueous membrane emulsion methods disclosed herein, wherein the composition contains >100 mg of spray-dried protein. In some embodiments, the non-aqueous membrane emulsion methods have >90% yield, and produce microparticles with a purity of >99% and that have >10% w/w loading, and <10% burst.

EXAMPLES

Example 1: Blank Microspheres Synthesis Via H/F Based Bulk Emulsion

Materials and Methods

Oil and aqueous-based emulsion system are frequently used for polymeric microparticle or nanoparticle synthesis, where hydrophobic polymer materials are dissolved in the organic phase and dispersed in an aqueous continuous phase. However, for water-soluble polymers, e.g. PEG, carboxymethyl cellulose (CMC), and polymers that readily hydrolyze in the presence of water include polyanhydrides, aliphatic polyesters with short mid-blocks like polylactic acid and certain poly (amino acids) like poly (glutamic acid), conventional aqueous-based emulsion systems are not ideal. The following examples demonstrate the utility of the disclosed H/F emulsion system for producing the above mentioned hydrolyzable or water-degradable polymeric microparticles. In some embodiments, those polymers are first dissolved in a hydrocarbon solvent, including polar solvents, e.g. acetonitrile, tetrahydrofuran and less-polar solvents, e.g. DCM, chloroform. Then this polymer solution is added into a continues phase, the fluorocarbon liquid, e.g. FC-40 with a FS, e.g. Picosurf 1. An emulsion is made through agitation, vortexing or other blending methods. The emulsion droplets are finally hardened into polymer spheres through evaporating or extracting the hydrocarbon solvents.

In a particular embodiment, for blank POE microspheres synthesis via H/F bulk emulsion, as illustrated in Scheme 1 (FIG. 1A), 200 μL of about 10%. 20%, 30% and 40% w/v POE in DCM were added to 2 mL FC-40 containing 0.5% w/w FS Pico-Surf™ 1 (Sphere Fluidics). Emulsification was achieved through vortexing. The emulsions droplets were lighter than the FC-40 and floated on top of the solution. Aliquots were taken and dropped on glass slides for microscope imaging. The microspheres were hardened with stirring under vacuum for 3 hours. The hardened polymer spheres in FC-40 were first vacuum filtered through 0.22 micron PES membrane. The FC-40 passed through the filter and microspheres retained. Then the microspheres were washed with additional FC-40 and dried completely under vacuum. In another example with the same process, about 30% w/v POE in DCM were used in hydrocarbon phase and about 0.01%, 0.1%, and 0.5% FS in FC40 were used in the fluorocarbon phase to evaluate the effect of FS concentration.

Results

Figure 1B:
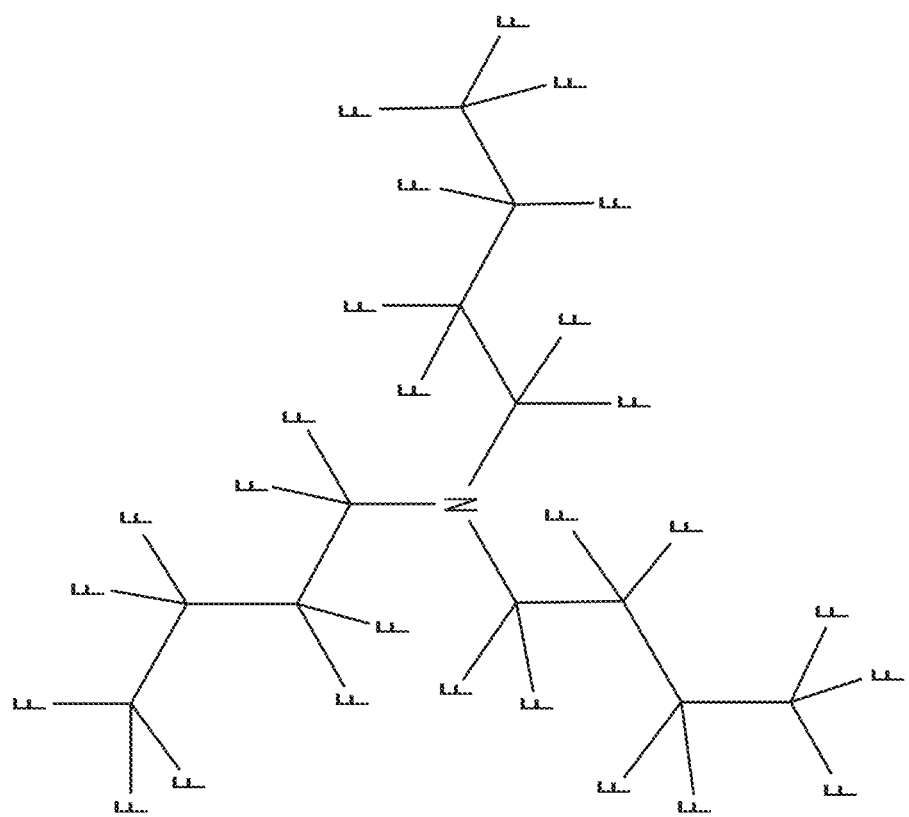
FIG. 1B shows the chemical structure for FC40.
Figure 1C:
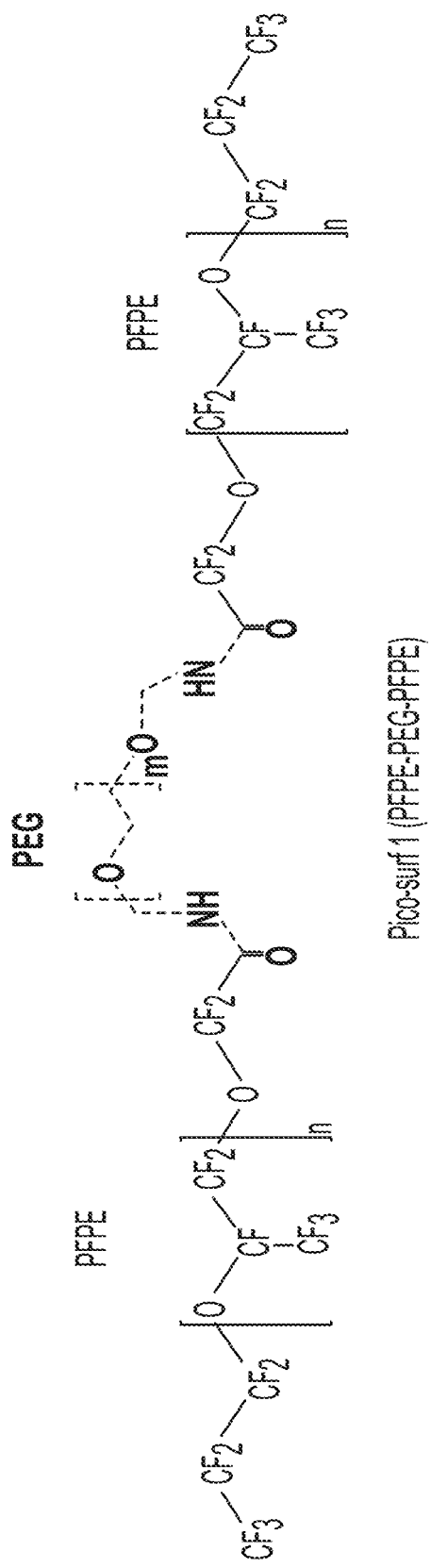
FIG. 1C shows the chemical structure for the fluorosurfactant PFPE-PEG-PFPE (Pico-Surf™ 1), a perfluoropolyether/poly(ethylene glycol) triblock copolymer. Pico-Surf™ 1 is commercially available, for example as 5% (w/w) in FC-40.

With the presence of FS, a hydrocarbon and fluorocarbon mixture were able to form H/F emulsion. In one example, DCM was dispersed in FC-40 (see structure of FC-40 in FIG. 1B) as H/F emulsions and PFPE-PEG-PFPE was used as FS (see structure of FS in FIG. 1C). Increasing concentrations of FS was added to the FC-40 fluorocarbon phase. Tests showed that 0.1-5% w/w FS was needed to prevent coalescing of the DCM droplets (FIG. 2A). If less than 0.1% w/w SF added, wider size distributions were observed. If no SF used. DCM droplets were not stable. The dispersed DCM droplet will quickly merge together, and two phases will soon separate. The results showed the necessity of using a sufficient amount of FS for producing stable H/F emulsions and stirring continuously during the hardening process to successfully produce polymer microspheres. (FIG. 2B).

Adding POE in the DCM and vortexed in FC-40 led to formation of POE containing droplets. Evaporation of DCM at ambient condition in an open container or under vacuum led to the droplet hardened to POE microspheres (FIGS. 2A and 2B). The sizes of microspheres were related with droplet sizes and POE content in the organic phase.

Higher POE concentration leads to larger microsphere size (Table 1).

TABLE 1

Microsphere sizes of the POE spheres produced with varying concentrations: of POE in DCM.

| Diameter | 10% w/v POE | 20% w/v POE | 30% w/v POE | 40% w/v POE |
|---|---|---|---|---|
| Dv(10) (µm) | 0.9 | 1.3 | 3.1 | 7.1 |
| Dv(50) (µm) | 2.7 | 7.2 | 17 | 34.8 |
| Dv(90) (µm) | 6.5 | 13.4 | 30.1 | 67.4 |

Example 2: Effect of Homogenization Speed

Materials and Methods

One (1) mL of 30% or 40% w/v POE in DCM were added to 9 mL of FC-40 with 0.5% (w/w) FS FC-40 and emulsified with a VWR Handheld homogenizer 200 with VWR 7 mm×95 mm saw-tooth generator probe, at one of three homogenizing speed, low (about 50% of full power), Middle (about 60% of full power), and high (about 70% of full power). The formed emulsions were stirred under vacuum. The microspheres formed were washed and dried under vacuum.

Results

Figure 3A:
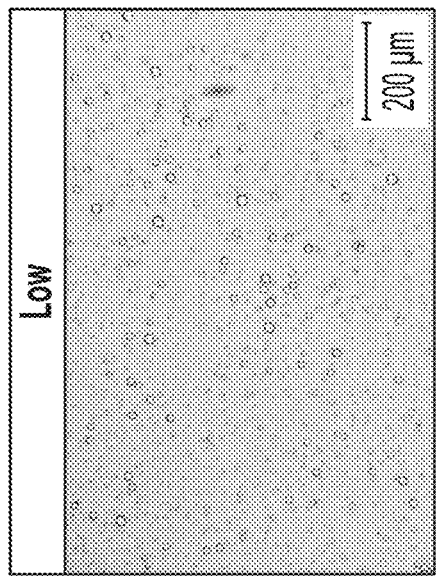
FIGS. 3A, 3B and 3C are micrographs of blank POE microsphere formed via H/F emulsion with low, middle, and high homogenizing speed.
Figure 3B:
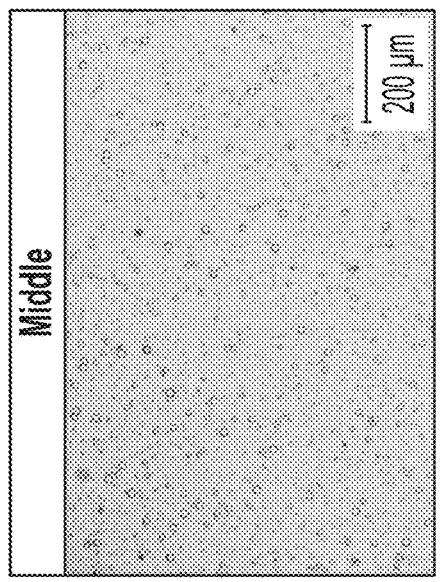
Figure 3C:
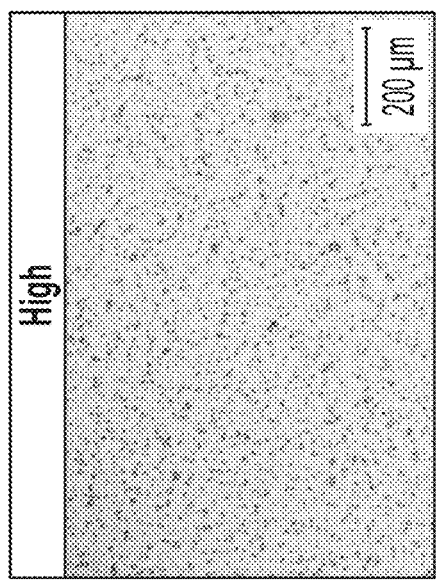
Figure 4:
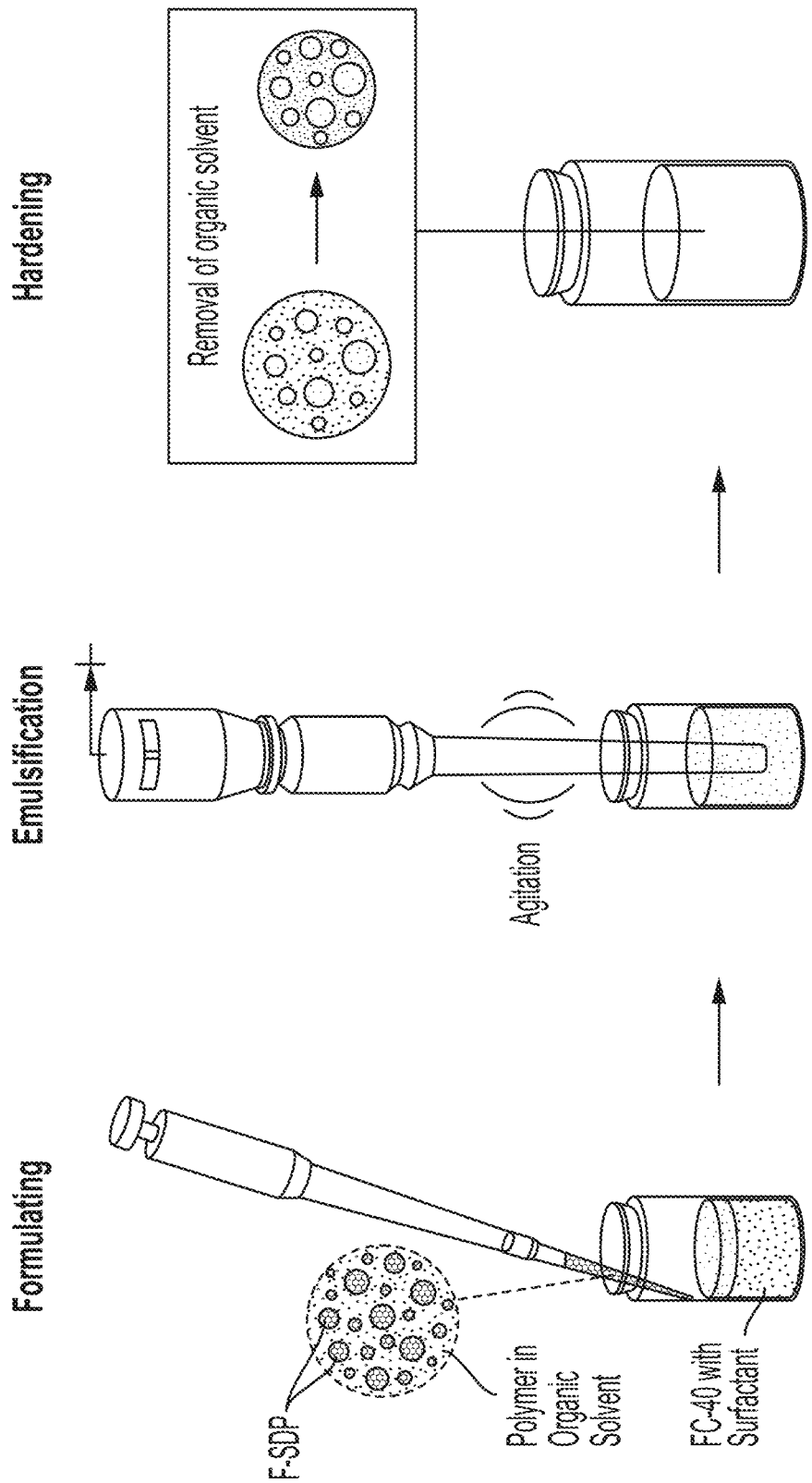
FIG. 4 (Scheme 2) is a diagram showing the process of SDP encapsulation in POE microspheres via S/H/F based bulk emulsion.
Figure 5:
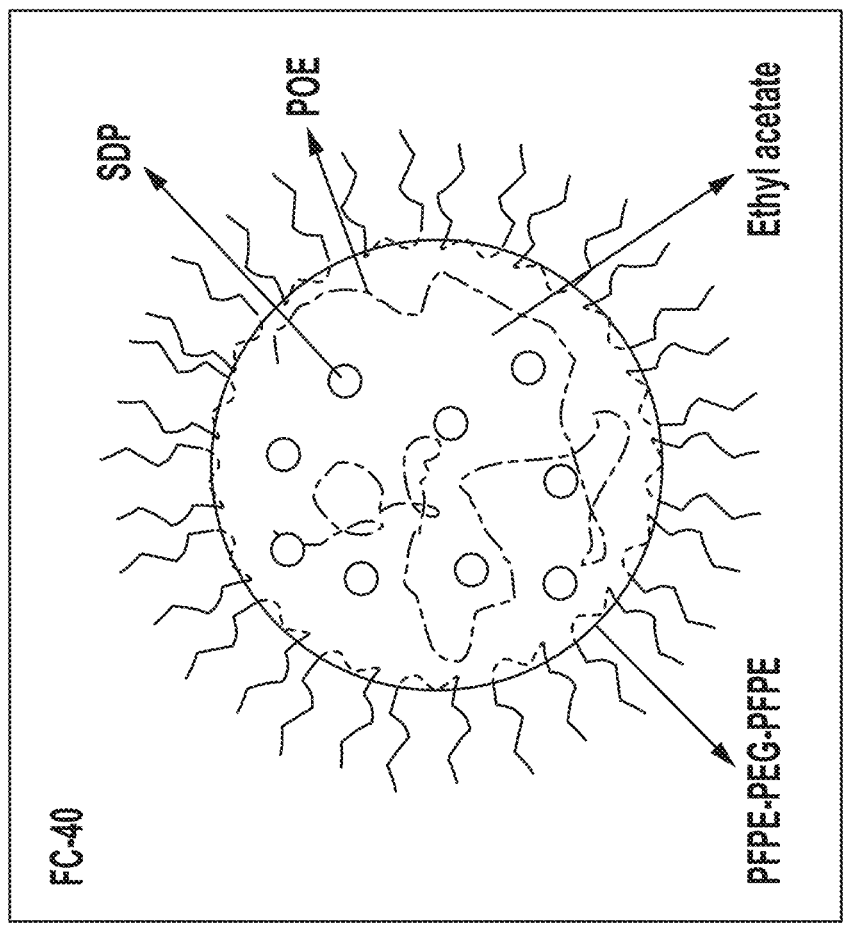
FIG. 5 (Scheme 3) is a diagram showing the hydrocarbon-in-fluorocarbon emulsion system for the encapsulation of protein SDP.
Figure 6B:
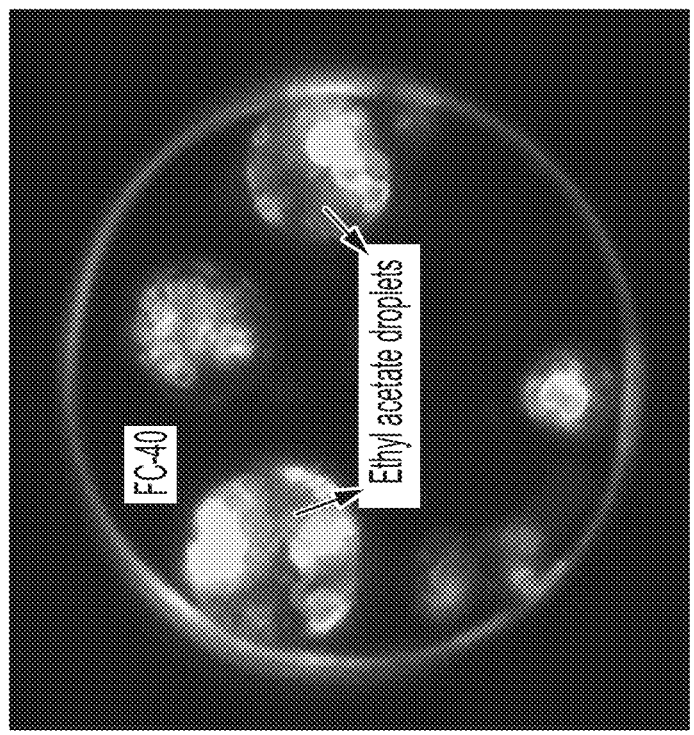
FIGS. 6A and 6B are fluorescence images of ethyl acetate droplets containing POE and fluorescent-labeled spray dried protein (F-SDP) dispersed in FC-40. Note that the F-SDP retained its original size and morphology within the droplet. Green fluorescent images are depicted in gray scale.
Figure 6A:
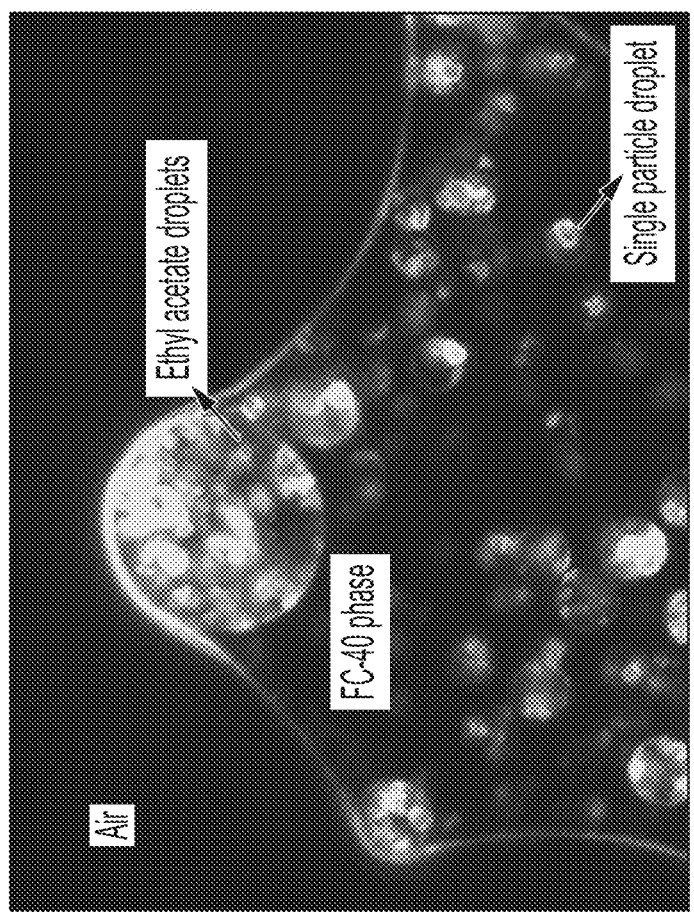
Figure 9:
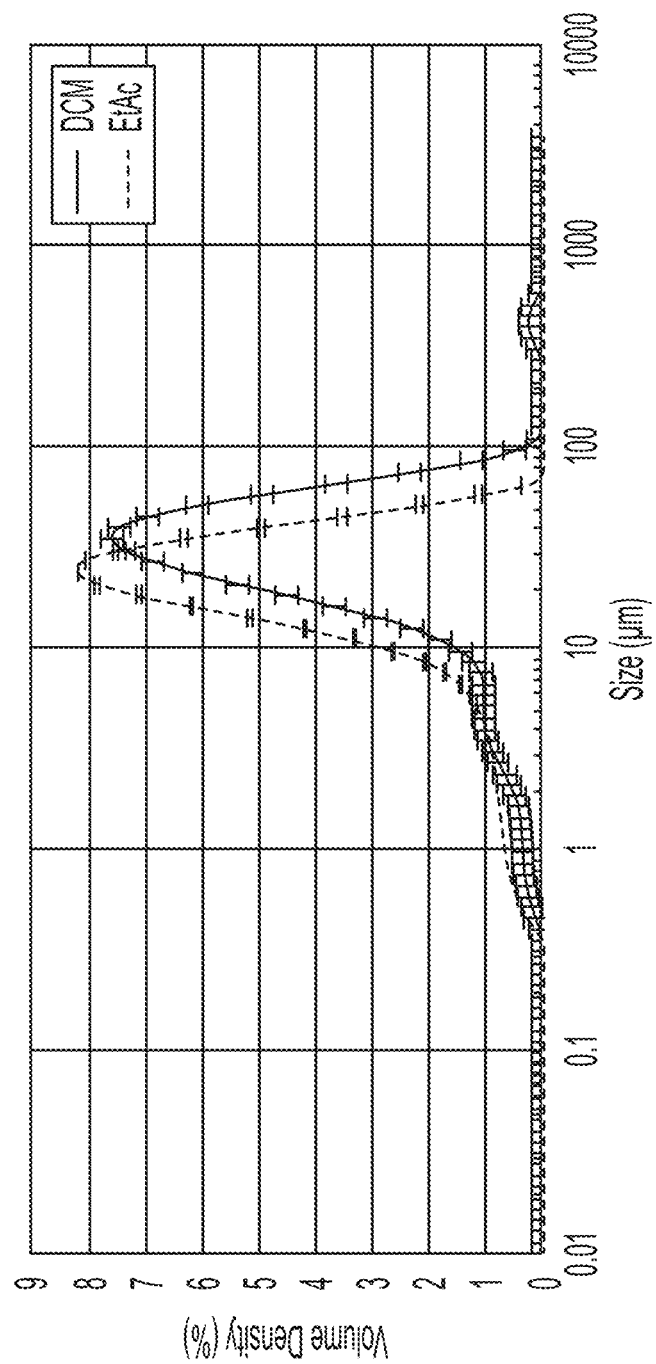
FIG. 9 is a line graph of volume density (%) versus size (μm) for microparticles produced using dichloromethane (DCM) or ethyl acetate (EtAc) in the non-aqueous emulsion methods.
Figure 11B:
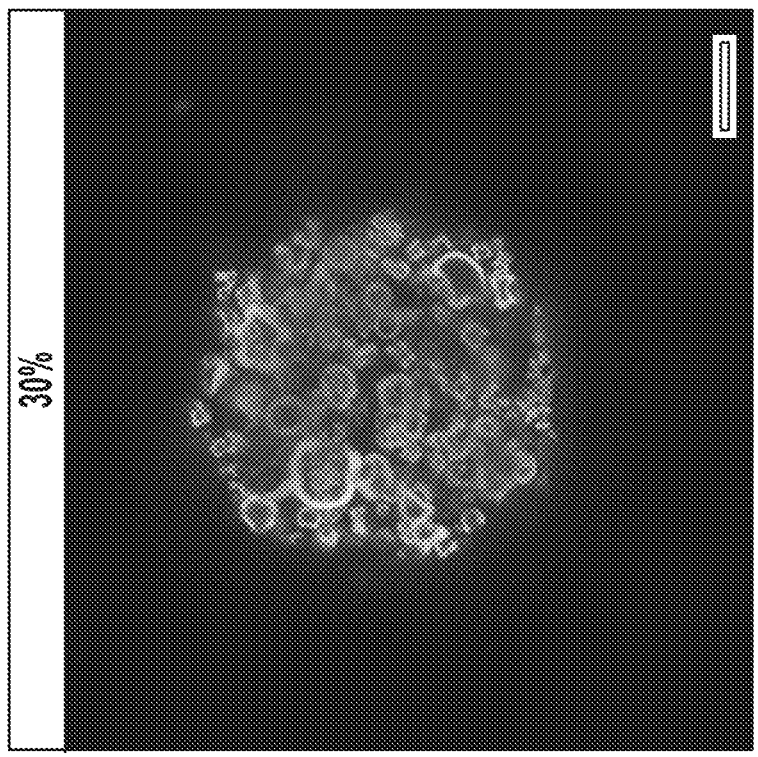
FIGS. 11A and 11B are representative fluorescence images of VEGF Trap F-SDP-encapsulated POE microspheres loaded with 10% and 30% w/w SDP respectively. Note that the F-SDP retained its original size and morphology within the droplet. Green fluorescent images are depicted in gray scale.
Figure 11A:
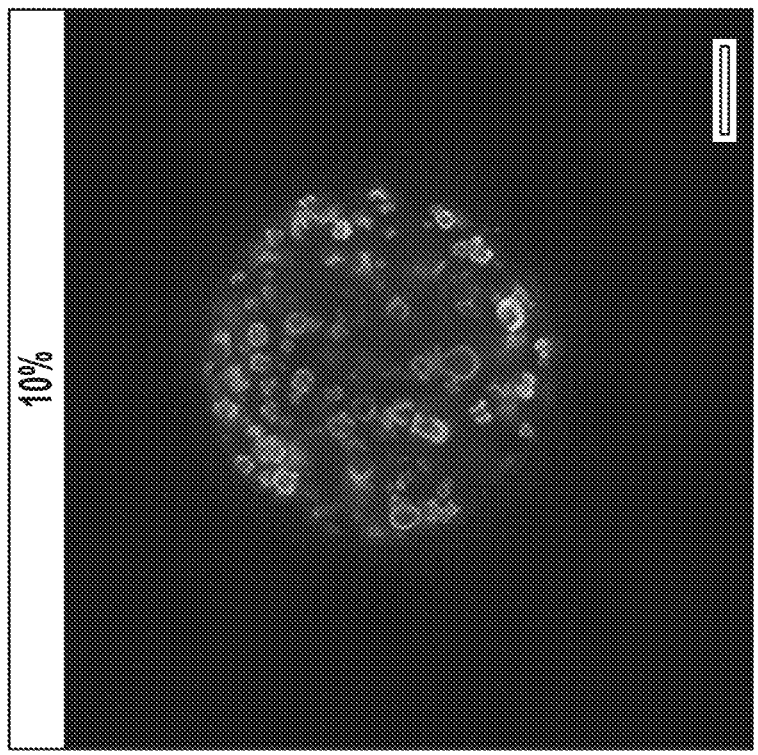
Figures 12A, 12B:
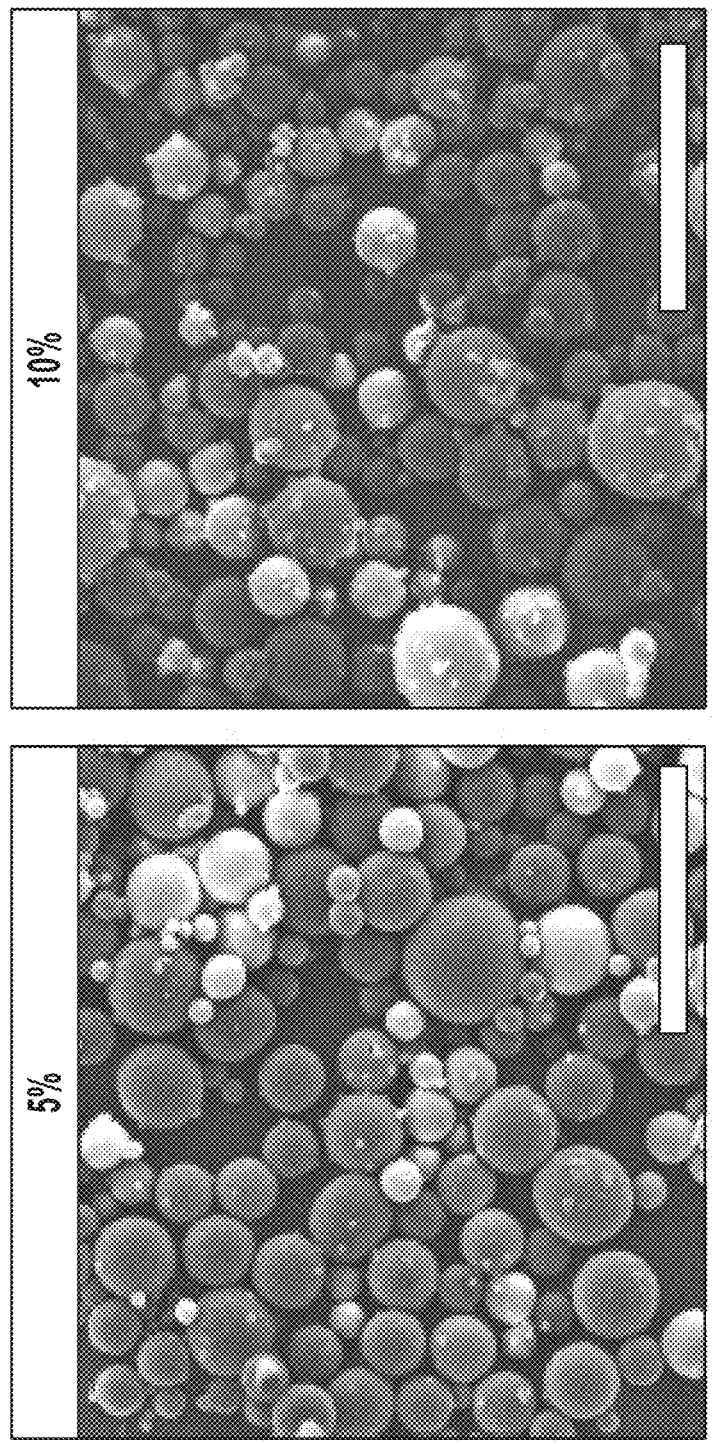
FIGS. 12A and 12B are scanning electron microscope (SEM) images of microparticles loaded with 5% w/w SDP and 10% w/w SDP.
Figures 13A, 13B:
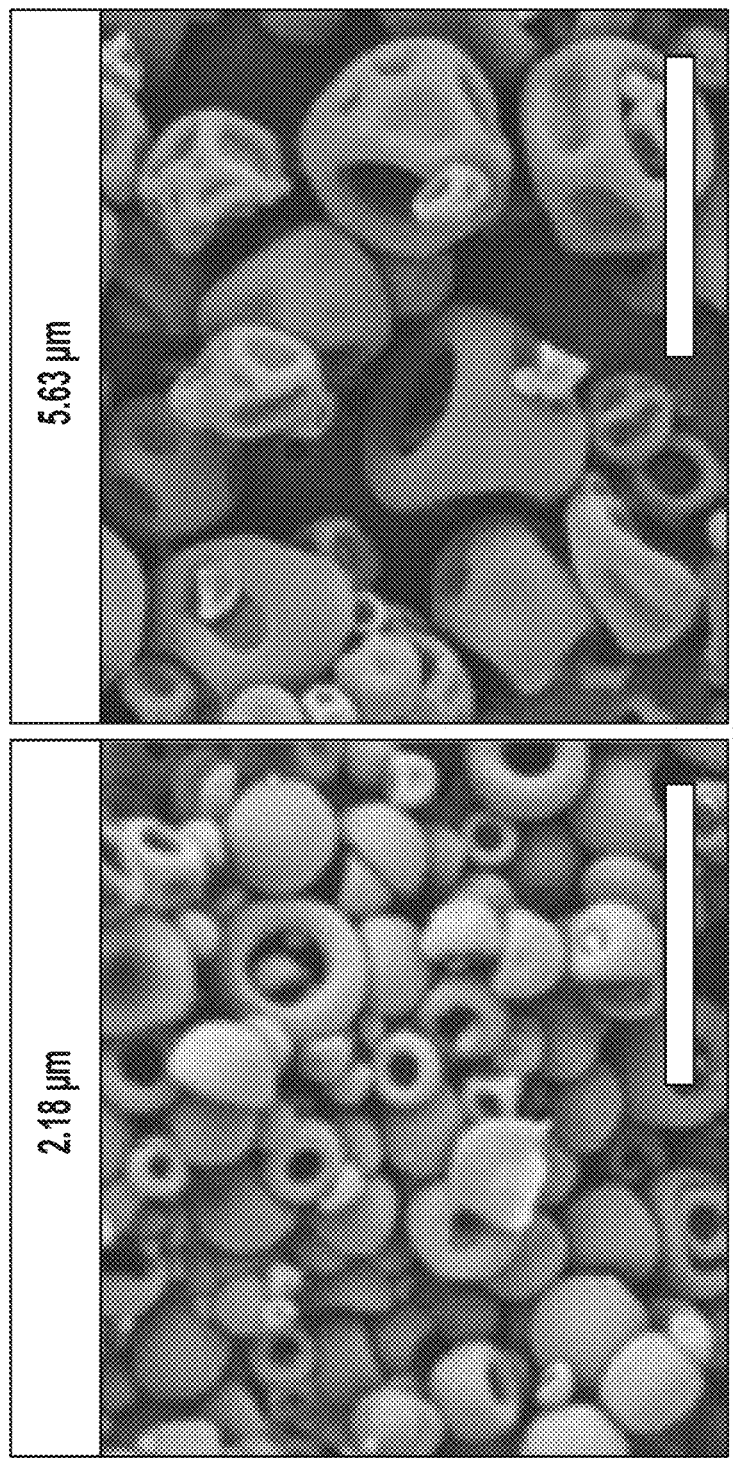
FIGS. 13A and 13B are SEM images of spray-dried protein with Dv50 of 2.18 μm and 5.63 μm.
Figures 14A, 14B, 14C:
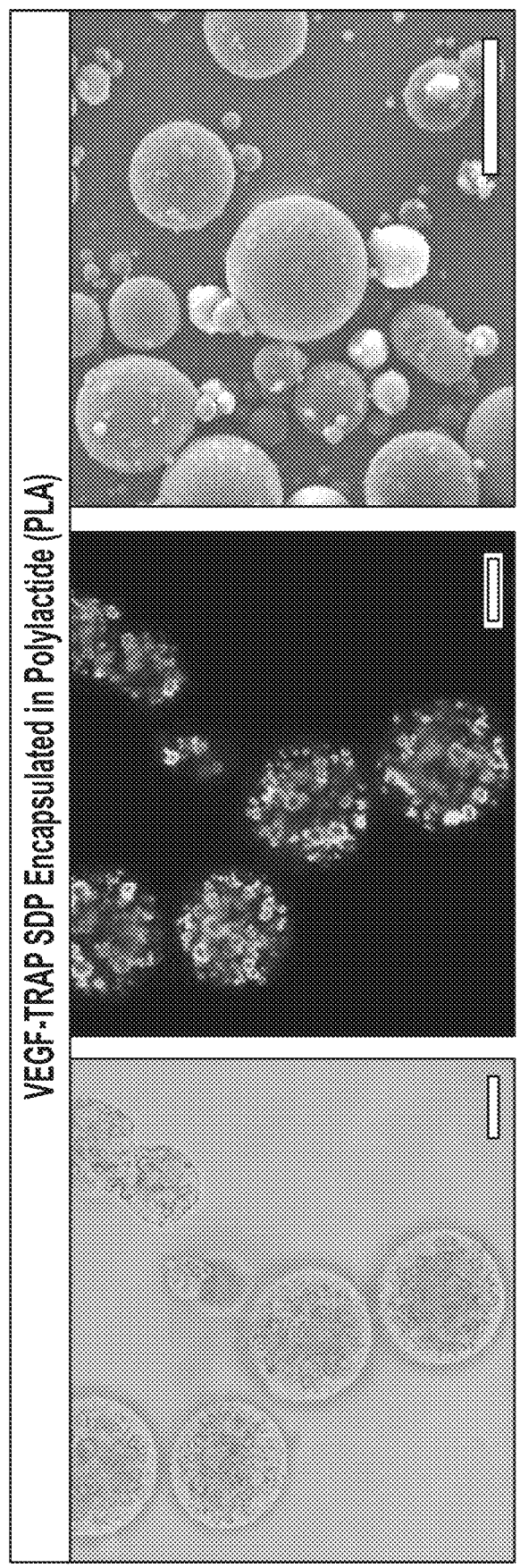
FIGS. 14A, 14B and 14C are bright field, fluorescence, and SEM images of VEGF-Trap F-SDP encapsulated in PLA microspheres. Green fluorescent images are depicted in gray scale in FIG. 14B.
Figure 15B:
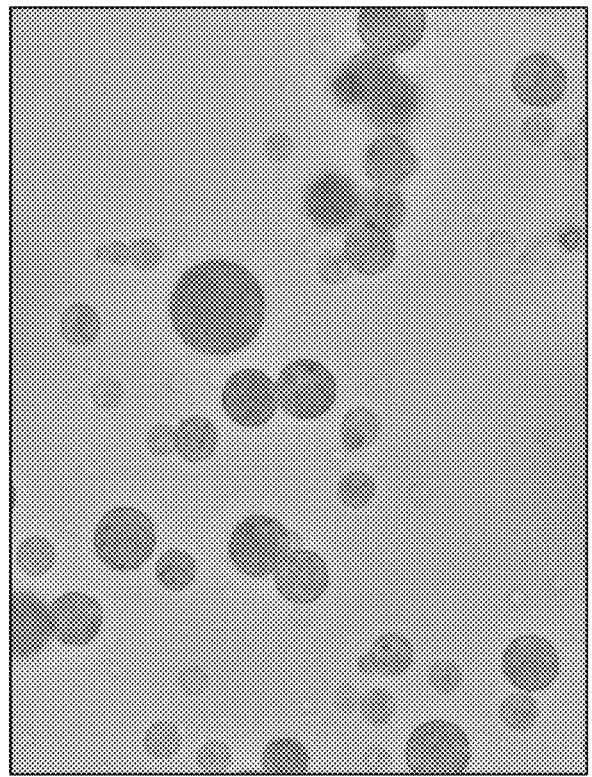
FIGS. 15A and 15B are bright field and fluorescence images of VEGF-Trap F-SDP encapsulated in PLGA microspheres. Green fluorescent images are depicted in gray scale in FIG. 15B.
Figure 15A:
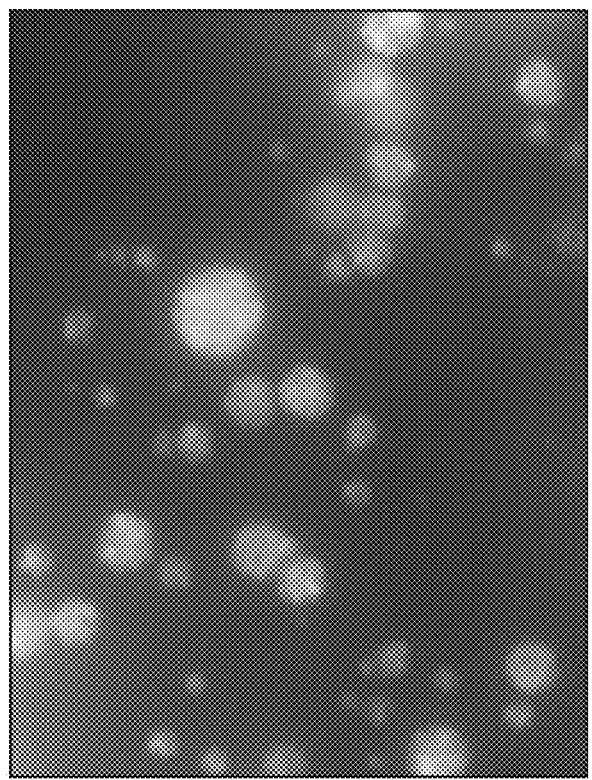

As illustrated in FIGS. 3A-C, for 30% POE, low homogenizing speed gave larger microsphere sizes while high homogenizing speed gave smaller sizes (Table 2). The 40% POE showed the same trend. These results show that tuning the homogenizing speed could control the microsphere size.

TABLE 2

Microsphere sizes of the POE spheres produced with varying homogenizing speed.

| Diameter | Low Speed | Middle Speed | High Speed |
|---|---|---|---|
| Dv(10) (µm) | 2.8 | 2.0 | 1.1 |
| Dv(50) (µm) | 16.1 | 13.5 | 5.4 |
| Dv(90) (µm) | 31.5 | 31.6 | 12.0 |

Example 3: General Procedures of Protein SDP Encapsulation in POE Microspheres Via S/H/F Based Bulk Emulsion Method Materials and Methods As illustrated in FIG. 4, a bulk emulsion synthesis can be divided into three steps, formulating, emulsification, hardening. The properties of the product will be different as different parameters used in these three steps. The general procedures are described as below:

For formulating, 10%-30% w/w of total solid weight VEGF Trap SDP (or fluorescent-labeled SDP (F-SDP) for fluorescence imaging) were dispersed in 500 μL ethyl acetate containing 10-35% w/v POE by vortexing and subsequent sonication for 5 min. Then these suspensions were added into 9.5 mL FC-40 with 0.1-0.5% w/w FS. Emulsification can be achieved through agitation, vortexing or homogenizing using a bench-top homogenizer. The structures of the emulsions are illustrated in FIG. 5. Immediately after emulsification, in-process aliquots were taken and dropped on glass slides for microscope imaging. The droplets were hardened on the slide through evaporation under ambient conditions. For hardening the microspheres, one of three methods were applied: (a) Stirring the solution at ambient condition for overnight in an open container and allowing evaporation of the ethyl acetate; (b) Stirring the solution under vacuum for at least 2 hours for a faster solvent evaporation; (c) adding NOVEC 7500, or a mixture of FC-40 and NOVEC7500 into the emulsion under stirring. The HFE acts as a co-solvent that help extracting ethyl acetate from the hydrocarbon phase into the fluorocarbon phase and enable a rapid hardening process (typically within minutes).

In the end, the hardened polymer spheres in FC-40 were first vacuum filtered through 0.22 μm PES membrane. The FC-40 passed through the filter and microspheres retained. Then the microspheres were washed with additional FC-40 and dried completely under vacuum.

The sizes of the microspheres were measured by laser diffraction analysis using a Malvern Mastersizer 3000 with liquid sampling by dispersing the product powder in 0.01% w/v PVA solution. The morphology of the product was measured using scanning electron microscopy (SEM).

To measure the protein content of the microsphere, a predetermined amount of microsphere was first dissolved in 200 μL of ethyl acetate and then extracted with 1 pure water, the aqueous phase was collected and centrifuged to remove turbid suspension. The protein purity and concentration were measured by SEC-UPLC.

To measure burst release, a predetermined amount microsphere was incubated in 1 mL of PBS at 37° C. for 1 hour. The mixture was centrifuged, and the supernatant was subjected to SEC-UPLC for protein concentration.

Results

Results above showed the formation if stable H/F emulsion with the presence of sufficient SF. This non-aqueous emulsion can successfully produce blank POE spheres. This anhydrous method was used again to incorporate SDP into POE microspheres. In one example, VEGF Trap F-SDP 10% w/w of total solid weight were introduced in the ethyl acetate (including 20% w/v POE) as a suspension and this suspension in FC-40 (containing 0.5% w/w FS) was blended through agitation and vortexing. Immediately after emulsification, aliquots were transferred on glass slides for microscopy imaging. As shown in FIGS. 6A and 6B, the ethyl acetate dispersed into droplets in FC-40, the SDP particles were clearly confined inside the ethyl acetate droplets. Contrary to the S/O/W system (data not shown) there was no sign of protein leaking into the fluorocarbon continuous phase. Importantly in this H/F system, the SDP particle in the droplet retained their original dimpled shape in the powder state. Since there was no water in H/F system to reconstitute SDP, and thus the SDP remained in its original solid particulate form. After hardening, POE microspheres containing single or multiple SDP particles can be clearly observed through bright filed and fluorescence microscope images (FIGS. 7A, 7B and 7C). After evaporation of hydrocarbon and fluorocarbon solvents on the glass slides, water was added to test the burst release and the quality of encapsulation. As shown in FIGS. 8A-D, after placing the microsphere product in water, the SDP-encapsulated POE microspheres retained their integrity. No immediate release of protein was observed, and the shape of SDP particles remained the same, which indicated that SDP particles were well protected by the polymer matrix and shielded from the aqueous environment. These results suggest that the H/F emulsion is an effective solution for encapsulating proteins and other hydrophilic drugs into polymeric matrices, and has the potential of achieving high encapsulation efficiency, high yield, while minimizing burst release—all of which are major challenges when using an aqueous-based W/O/W or S/O/W methods.

The procedures disclosed here are examples of using S/H/F non-aqueous based bulk emulsion method for protein SDP encapsulation in POE microspheres. The method is reproducible, scalable, and tunable. By varying the parameters in the formulation and process, the product properties can be tuned and controlled. The effects of some of those parameters are disclosed in Example 4.

Example 4: Effect of Hydrocarbon Solvents

Materials and Methods

Microparticles were produced as described in Example 2 using dichloromethane or ethyl acetate as the hydrocarbon. 35% w/v POE in DCM and 35% w/v POE in ethyl acetate were prepared. Ten percent (10%) w/w of total solid weight of protein powder were suspended in 0.5 mL of the POE solution in DCM or in ethyl acetate. These suspensions were transferred into 9.5 mL of FC-40 containing 0.5% w/w FS in 20 mL scintillation vial. These mixtures were homogenized to generate emulsion and stirred under house vacuum for 1.5 hours. The formed microspheres were isolated by filtering, washed with FC-40, and dried under vacuum.

Results

FIG. 9 shows size distribution of microparticles produced using the same formulation and process condition except the type of hydrocarbon solvent, either dichloromethane or ethyl acetate. Microparticles produced using either hydrocarbon show encapsulation of spray-dried protein. Using dichloromethane generates larger microparticles. See Table 3 below. The results suggested that under the same formulation and process condition, using different hydrocarbon solvent leads to microsphere in different sizes. DCM produced larger microsphere size than ethyl acetate. Therefore, a hydrocarbon solvent can be chosen deliberately to control microsphere size.

TABLE 3

Microparticle sizes of the SDP loaded POE spheres produced with DCM or ethyl acetate.

| Diameter | DCM | EtAc |
|---|---|---|
| Dv(10) (μm) | 5.2 | 3.2 |
| Dv(50) (μm) | 30.7 | 21.2 |
| Dv(90) (μm) | 64.9 | 42.3 |

Example 5: Effect of Protein Loading Amount

Materials and Methods

Microparticles were produced as described in Example 2 varying only the protein loading amount. Thirty-five percent (35%) w/v POE in DCM were prepared. 5%, 10% and 30% w/w of total solid weight of protein powder was suspended in 0.5 mL of the POE solution in DCM. These suspensions were transferred into 9.5 mL of FC-40 containing 0.5% w/w FS in 20 mL scintillation vial. These mixtures were homogenized for about 1 min to generate emulsion and then 6 mL of 1:1 v:v mixture of Novec7500 and FC-40 were added into the emulsion within one minute. Then after stirring for another minute, the formed microspheres were isolated by filtering, washed with FC-40 and dried under vacuum.

Results

As shown in Table 4, increasing the amount of protein powder in the formulation yielded larger POE microparticle size measured by laser diffraction analysis, and also yielded increased protein loading in the final POE microsphere products observed via protein extraction experiment, brightfield and confocal fluorescent microscopy. Brightfield images for 30% w/w protein powder loading showed darker and less transparent microspheres than 10% w/w protein powder, indicating more drug was encapsulated in the microsphere product (FIGS. 10A and 10B). Representative confocal images confirmed that the SDP was encapsulated in its original form in the POE matrix from cross sectional views of the microspheres (FIGS. 11A and 11B). More SDP particles were observed in the 30% w/w loading microspheres. Again, the SDPs encapsulated retained their original dimpled shapes indicating they were intact during the whole fabrication process.

TABLE 4

Microparticle sizes of the SDP loaded POE spheres produced with varying SDP loading.

| Diameter | 5% w/w SDP loading | 10% w/w SDP loading | 30% w/w SDP loading |
|---|---|---|---|
| Dv(10) (μm) | 4.9 | 5.2 | 17.1 |
| Dv(50) (μm) | 20.6 | 30.7 | 40.7 |
| Dv(90) (μm) | 43.0 | 64.9 | 81.3 |

FIGS. 12A and 12B are scanning electron microscope (SEM) images of microparticles loaded with 5% w/w SDP and 10% w/w SDP.

Example 6: Design of Experiments (DOE) on Encapsulation SDPs into POE Microspheres Using H/F Bulk Emulsification Materials and Methods A DOE study was performed to evaluate the impact of critical factors of the synthesis in a designed space on the properties of final products. Ten runs in the designed experiment were performed following a general procedure described in Example 2. Protein powder loading, protein powder particle size (Dv (50) size sizes are 2.2 um and 5.6 um, see SEM images in FIGS. 13A and 13B, respectively), polymer concentration, and HFE concentration were varied while the following formulation and process conditions were kept constant. e.g. volume of hydrocarbon and fluorocarbon phase, homogenization speed, FS concentration (Table 5.). Measured responses including microsphere sizes (Dv50, Span by laser diffraction), encapsulation efficiency, burst release at 1 hour 37° C., SEM images.

Results

The results of the DOE are summarized in Table 5.

TABLE 5

Experimental design and measured responses of SDP encapsulation DOE study.

| | Experimental Design | | | | Measured Responses | | | |
|---|---|---|---|---|---|---|---|---|
| Run # | Target Protein Powder Loading (%) | [POE] (%; w/v) | [HFE] (%; w/v) | Protein particle Size (DV50; um) | Microsphere size (DV50, um) | Span | Product SDP loading (%)* | Protein burst** release (%) |
| 1 | 25 | 25 | 25 | 5.6 | 23.3 | 1.2 | 25.3 | 103 |
| 2 | 25 | 35 | 25 | 2.2 | 27.4 | 1.4 | 26.7 | 99 |
| 3 | 5 | 35 | 25 | 2.2 | 20.6 | 1.8 | 6.1 | 10 |
| 4 | 5 | 25 | 25 | 5.6 | 17.9 | 1.48 | 5.3 | 29 |
| 5 | 15 | 25 | 25 | 2.2 | 18.1 | 1.50 | 15.4 | 52 |
| 6 | 5 | 35 | 35 | 5.6 | 21.6 | 1.74 | 3.9 | 15 |
| 7 | 5 | 25 | 35 | 2.2 | 19.4 | 1.55 | 4.1 | 9 |
| 8 | 15 | 35 | 35 | 5.6 | 25.3 | 1.39 | 13.8 | 78 |
| 9 | 25 | 25 | 35 | 2.2 | 21.5 | 1.30 | 20.8 | 116 |
| 10 | 25 | 35 | 35 | 5.6 | 35.2 | 1.517 | 23.8 | 91 |

*Microsphere were dissolved in ethyl acetate and protein were extracted using water and quantified using SEC-UPLC.
**Microsphere were incubated in PBS at 37° C. for 1 hour. Released protein were quantified using SEC-UPLC.

Custom designed DOE fitting on microsphere size (with $R^2=0.76$) revealed the major effects of protein powder loading and POE concentration (with p-value <0.05, see correlation results in Table 6.). In addition, fitting on burst release ($R^2=0.92$) shows that only protein powder loading significantly affects burst release (with p-value <0.05, see correlation results in Table 7). The results suggest that increasing the protein powder amount in formulation will lead to higher payload in the final product, but it will also increase the burst release percentage. The burst release is likely caused by surface adsorbed protein particles. The maximum amount of protein powder internalized in the polymer microsphere is determined by the physical space for a given microsphere size. Simply increasing the protein powder concentration in the formulation suspension will not increase drug encapsulation beyond a certain threshold which was about 30% w/w in this example.

TABLE 6

Correlations of factors with microsphere size.

| Term | Estimate | Std Error | T Ratio | Prob > \|t\| | VIF |
|---|---|---|---|---|---|
| Intercept | 23.03 | 0.924421 | 24.91 | <.0001* | |
| SDP Loading (%)(5, 25) | 3.4875 | 1.033534 | 3.37 | 0.0118* | 1 |
| [Polymer] (%; w/v)(25, 35) | 2.99 | 0.924421 | 3.23 | 0.0144* | 1 |

TABLE 7

Positive Correlation of SDP loading with burst release.

| Term | Estimate | Std Error | T Ratio | Prob > \|t\| | VIF |
|---|---|---|---|---|---|
| Intercept | 63.190484 | 4.008836 | 15.76 | <0.0001* | |
| SDP Loading (%)(5, 25) | 43.17019 | 4.482015 | 9.63 | <0.0001* | 1 |

Example 7. Application of S/H/F Emulsion-Based Encapsulation Method to Different Proteins The disclosed H/F based emulsion system and process can be a platform technology that is applicable for different polymers and therapeutic proteins. In a specific example of the invention, a protein powder of a recombinant IgG4 (MW ~145 kDa), a protein powder of recombinant IgG1 (MW ~146 kDa), or a protein powder of a recombinant fusion protein (MW ~64 kDa) were incapsulated into POE microspheres respectively through the same process as in Example 2. The results are summarized in Table 8. The amount of encapsulated protein powder in the microsphere product was determined through the extraction assay and matched the target value. The protein purity retained for the recombinant fusion protein. IgG1 or slightly decreased for IgG4 (less than 2%) after the encapsulation process indicate a good process compatibility.

TABLE 8

Results of SDP with different types of proteins encapsulated in POE microspheres via S/H/F emulsions.

| Protein type | Protein purity in the SDP by SEC-UPLC | Target Solid Loading in Formulation (%) w/w | Encapsulated Protein Powder % w/w by Extraction | Encapsulated protein % w/w* | Percentage of Protein burst released** | Encapsulated Protein purity by SEC-UPLC |
|---|---|---|---|---|---|---|
| Recombinant Fusion Protein | 97.8% | 15 | 13.7 | 8.6 | 44% | 98.2% |
| IgG4 | 99.4% | 15 | 15.0 | 12.0 | 24% | 97.6% |

TABLE 8-continued

Results of SDP with different types of proteins encapsulated in POE microspheres via S/H/F emulsions.

| Protein type | Protein purity in the SDP by SEC-UPLC | Target Solid Loading in Formulation (%) w/w | Encapsulated Protein Powder % w/w by Extraction | Encapsulated protein % w/w* | Percentage of Protein burst released** | Encapsulated Protein purity by SEC-UPLC |
|---|---|---|---|---|---|---|
| IgG1 | 98.4% | 15 | 16.5 | 11.7 | 22% | 98.9% |
| IgG1 (alternate formulation) | 96.8% | 15 | 13.7 | 8.9 | 44% | 97.4% |

*Microsphere were dissolved in ethyl acetate and protein were extracted using water and quantified using SEC-UPLC.
**Microsphere were incubated in PBS at 37° C. for 1 hour. Released protein were quantified using SEC-UPLC.

Other biodegradable polymers e.g. PLGA and PLA are also used in the H/F based emulsion. In a specific example of the invention, through a similar process disclosed in Example 2, fluorescent-labeled VEGF Trap F-SDP were encapsulated in PLGA (lactide:glycolide 50:50, Mw 42-65 kDa, Sigma Aldrich) and PLA (alkyl ether terminated, Mw 18,000-28,000, Sigma Aldrich) microspheres, respectively. Other polymer ratios and molecular weights also can be employed. Brightfield and fluorescent microscope images indicated the protein powder was successfully encapsulated inside of the polymer microspheres (FIGS. 14A-C for PLA and FIGS. 15A-B for PLGA).

Example 8: Membrane Non-Aqueous Emulsion

Microparticles were produced using membrane emulsion using the materials described in Table 9.

TABLE 9

| Material | Description | Manufacture | Lot/Item # |
|---|---|---|---|
| Spray Dried Fluorescently labelled Alexa-488 VEGF Trap | Feed solution, containing 1% of Alexa-488 labeled VEGF Trap | Regeneron, NY | |
| Dichloromethane | Organic solvent anhydrous ≥99.8 | Sigma Aldrich | 270997-1L |
| FC-40 | Fluorinert™ FC-40 | Sigma Aldrich | F9755 |
| PVA | Polyvinyl alcohol, 146K-186K 87-89% hydrolyzed | Sigma Aldrich | 363103-500G |
| Pico-Surf 1 | Fluorosurfactant | Sphere Fluidics | C014 |

Membrane emulsification (ME) is a relatively new technique for the highly controlled production of particulates that allows good size control and narrow size distribution. To date, many different types of membrane have been developed for ME including Shirasu Porous Glass (SPG), cellulose acetate, polymer, anodic porous alumina, and silicon microchannels. For the disclosed processes, it was found that a stainless steel membrane with laser drilled pores suited the purpose best and the commercially available equipment by Micropore Technologies (Redcar, UK) enabled the laboratory research process and also scaling-up to GMP manufacturing. Several important features of the membrane technology include: 1. Tightly controlled membrane pore size allows all the SDP particles below a limit passing through the membrane; 2. The straight tubular channel with no tortuous paths reduce the tendency of channel blocking by SDP; 3. Fluorophilic membrane coating provide good compatibility with the production of hydrocarbon-in-fluorocarbon (H/F) emulsion. In addition, the stainless membranes are robust, easy to clean, and sterilizable.

For one experiment, blank POE microspheres (RS001-Batch 1) or protein-encapsulated POE microsphere (RS001-Batch 2) were produced through membrane emulsification using conventional aqueous-based emulsion system. The production parameters are listed in Table 10. In Batch 1, 10% w/w POE solution in DCM was used as the dispersed phase and 1% polyvinyl alcohol (PVA) was used as continues phase to produce blank POE microspheres. In Batch 2, microencapsulation was performed for VEGF Trap SDP (containing 1% Alex488-labeled VEGF Trap) with size D50=2.2 (D10=1.0, D90=3.8, Span=1.24). SDP was added into 10% w/w POE solution in DCM with SDP:POE=9:1 by weight. The mixture was vortexed and sonicated for 5 min in a sonication bath to make a homogeneous suspension. The SDP suspension was immediately loaded into a 10 mL BD syringe and fed to the LDC-1 dispersion cell at a rate of 0.8 mL/min driven by a syringe pump. The emulsion was generated when the organic phase passing thorough the membrane with 30 um pores under stirring using 10V DC power (about 1,015 rpm depending on viscosity). The formed emulsion was transferred to an uncapped beaker and hardened into microspheres at ambient condition without stirring overnight. The microsphere products were finally washed with MilliQ water on a vacuum filter and dried under vacuum overnight.

TABLE 10

Parameters used in Batch 1 and Batch 2, membrane emulsification using conventional aqueous emulsion system.

| | Batch 1 (POE only, O/W) | Batch 2 (POE + SDP, S/O/W) |
|---|---|---|
| Membrane | Hydrophilic, uncoated membrane, 30 um pore size. | |
| Continuous phase | 1% PVA water solution, 100 mL | |
| Dispersed phase | POE 10% w/w in DCM, 3 mL | POE 10% w/w in DCM + SDP, SDP:POE = 9:1 w/w, 3 mL |
| Feeding rate | 1 mL/min | 0.8 mL/min |
| Stirring rate | 6V DC (~552 rpm) | 10V DC (~1015 rpm) |
| Hardening condition | Ambient, non-stirring. | |
| Washing and drying | Wash with MQ water and dry under house vacuum | |

Figure 16:
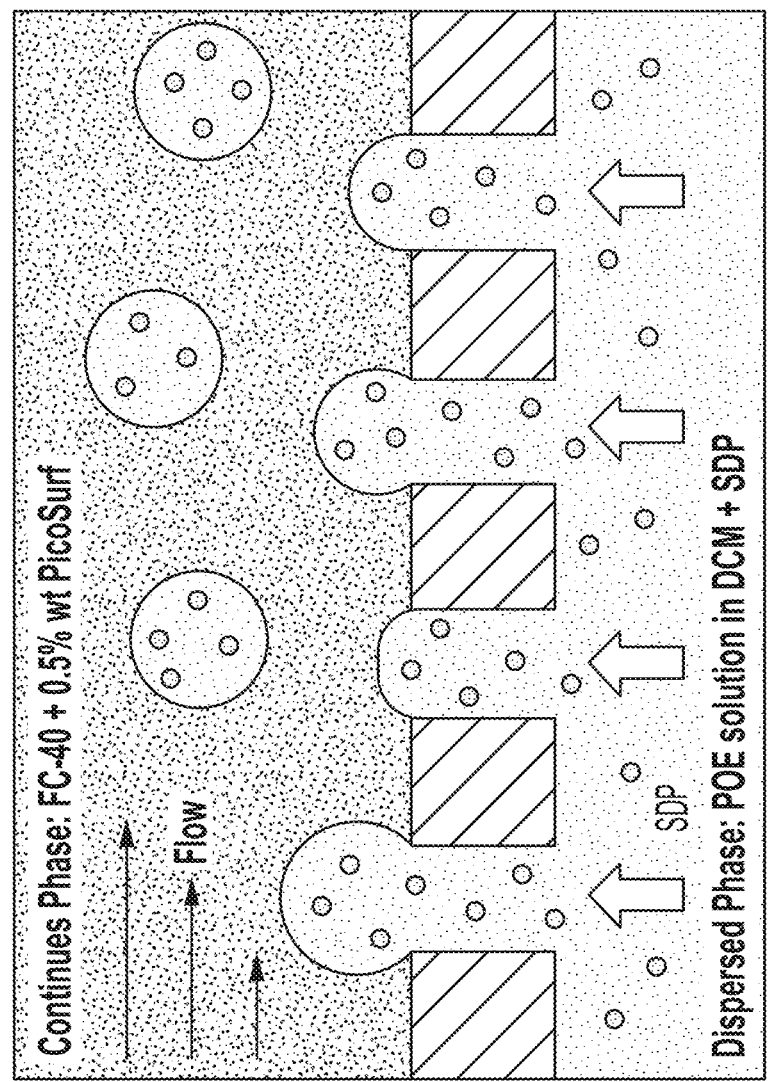
FIG. 16 is a diagram showing the formation of SDP suspension emulsion droplet when the suspension is infused through a porous membrane into a hydrocarbon continuous phase.
Figure 17:
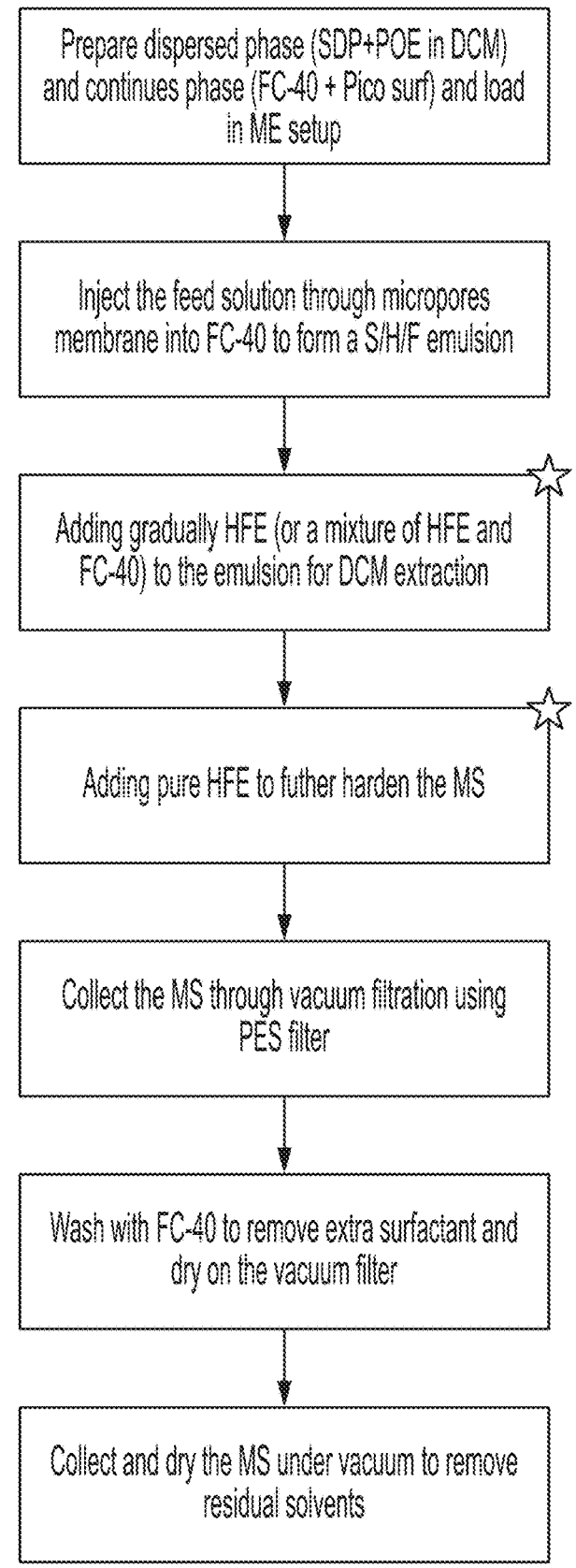
FIG. 17 is a diagram of an exemplary method for producing microparticles using membrane emulsion. Steps marked with stars to indicate the steps that prevent flocculation and aggregation of the microparticle product.

For another experiment, blank POE microspheres (Batch 3) or protein-encapsulated POE microsphere (Batch 4) were produced through membrane emulsification using novel non-aqueous hydrocarbon-in-fluorocarbon emulsion system. The production parameters are listed in Table 11. In Batch 4a the above-mentioned VEGF Trap SDP (containing 1% Alexa488-labeled VEGF Trap) was added into a hydrocarbon solvent, DCM, containing bio-degradable or bio-erodible polymer POE. The mixture was vortexed and sonicated to form a homogenous suspension. The SDP suspension was immediately loaded into a syringe and fed into the LDC-1 dispersion cell by a syringe pump. The suspension was infused through a porous membrane having a pore size larger than the protein powder particles into a Fluorocarbon (e.g. FC-40) continuous phase containing a fluorosurfactant (e.g. Pico-Surf 1) to form a hydrocarbon-in-fluorocarbon emulsion (illustrated in FIG. 16). The subsequent microsphere hardening was achieved through removing the hydrocarbon solvent from the formed emulsion droplets by adding a hydrofluoroester, NOVEC 7500, into the fluorocarbon as a cosolvent. The hardened microspheres were collected and washed with FC-40 to remove extra fluorosurfactant and dried using vacuum filtration containing a PES filter. Finally, the product was dried under vacuum to remove residual solvents. The flow-chart of the whole process is illustrated in FIG. 17.

TABLE 11

Parameters used in study RS002 membrane emulsification using anhydrous hydrocarbon -in-fluorocarbon emulsion system.

|  | Batch 3 (POE, H/F) | Batch 4 (SDP + POE, S/H/F) |
|---|---|---|
| Membrane | Fluorophilic-coated membrane, 30 um pore site | |
| Continuous phase | FC-40, 0.5% w PicoSurf, 50 mL | |
| Dispersed phase | POE 20% w/w in DCM,, 3 mL | POE 20% wlw in DCM, SDP:POE = 9:1 w/w, 3 mL |
| Feeding rate | 0.8 mL/min | 0.5 mL/min |
| Stirring rate | 8V DC | 550 8V DC (~rpm) |
| Hardening condition | | After emulsion formed, Adding HFE/FC-40 = 1:1 v/v, 40 mL. Then add pure HFE 10 mL. |
| Washing and drying | Wash with FC-40 on vacuum filter and dry under house vacuum | |

Results

Figure 18:
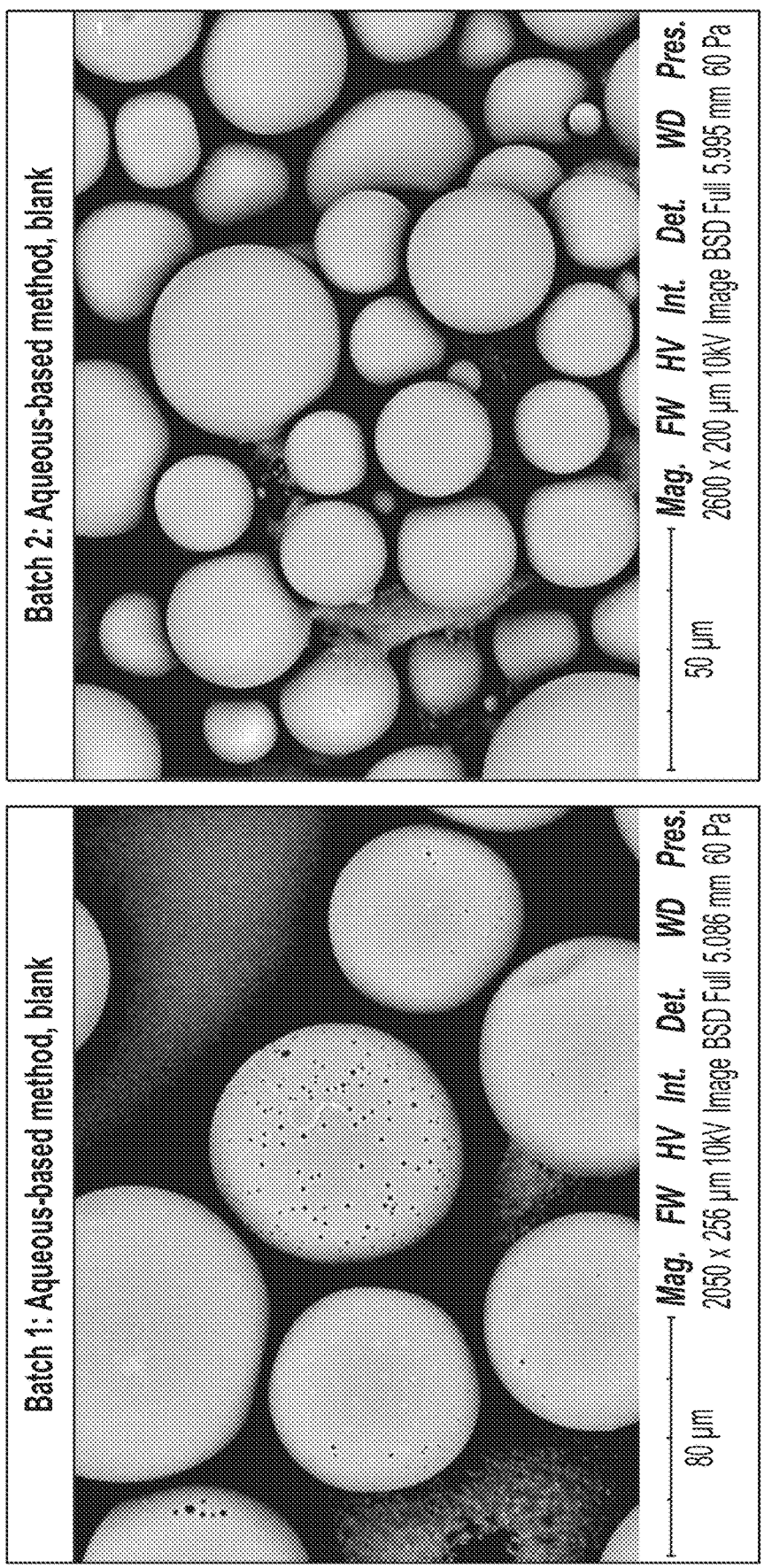
FIG. 18 contains SEM images of microspheres produced using aqueous and non-aqueous emulsion methods and show that the microspheres have pores and water channels using the aqueous method while have smooth surface using non-aqueous methods.

As displayed in FIG. 18, the SEM images of blank POE microspheres fabricated via the conventional aqueous-based emulsion system (Batch 1) and via non-aqueous-based emulsion system (Batch 3) show that both methods provide spherical microparticles but with different surface morphology. The aqueous-based method resulted in highly porous surface due to the present of water in the process, while the non-aqueous-based method resulted in smooth microsphere surface without clear pores due to the completely anhydrous process.

Figure 19:
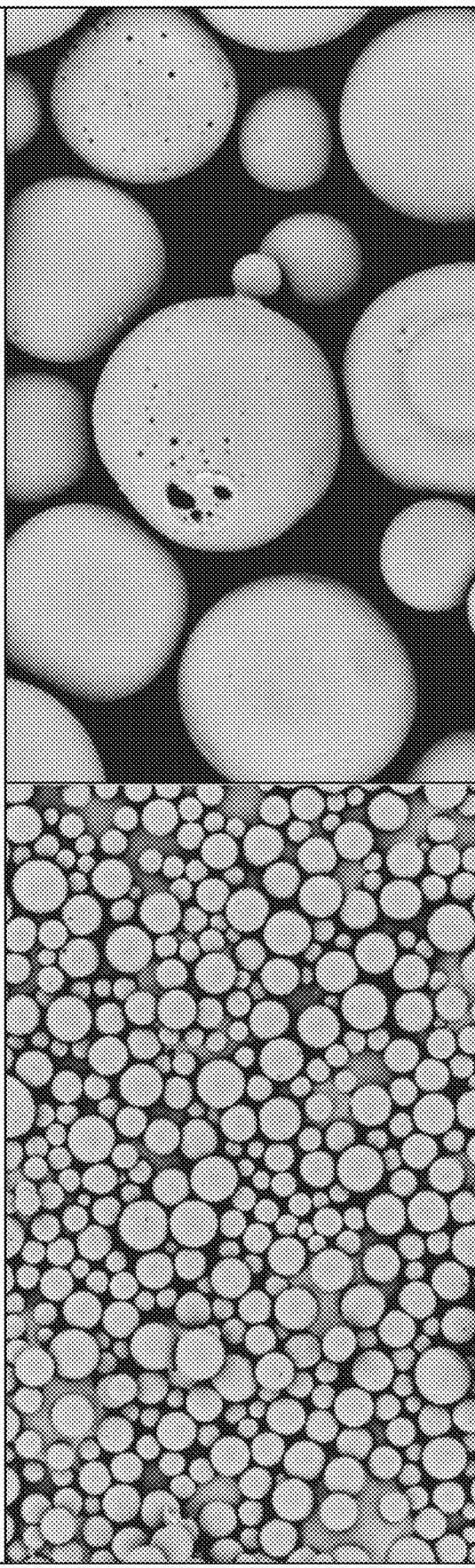
FIG. 19 contains SEM images of protein-encapsulated microspheres produced using aqueous and non-aqueous emulsion methods.
Figure 19:
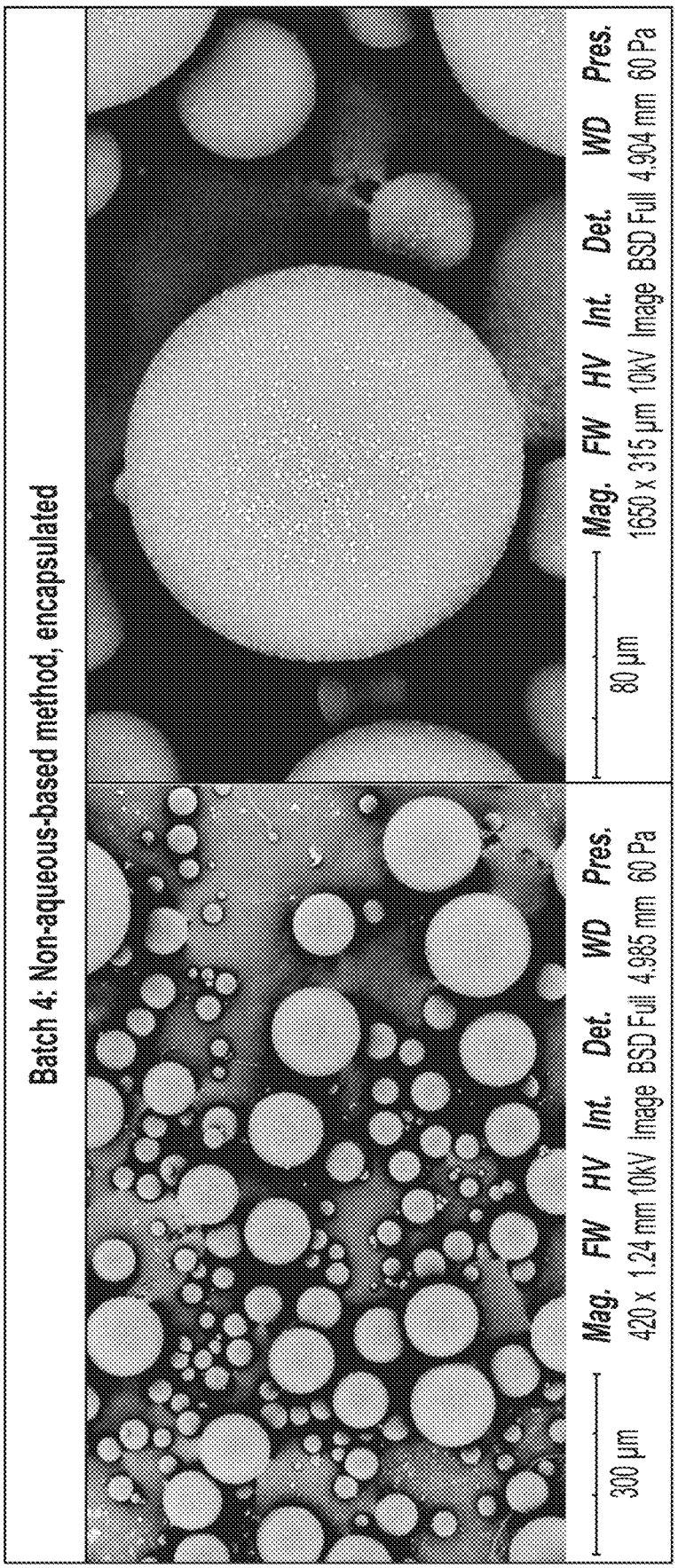

For microencapsulation of VEGF-Trap SDP into the POE microspheres, comparison of results from both methods are shown in FIG. 19. Water-based membrane emulsification (Batch 3) provided good monodispersed microspheres, but the surface is highly porous and with water channels. The monodispersity of microsphere from non-aqueous membrane emulsification is worse than the aqueous version but can be further improved by adjusting process parameters. In addition, many SDP are observed embedded on the surface of the POE microspheres. These surfaces located SDPs may contribute to the burst release of proteins after the microspheres are incubated in buffers (Tables 11 and 12).

Figure 20:
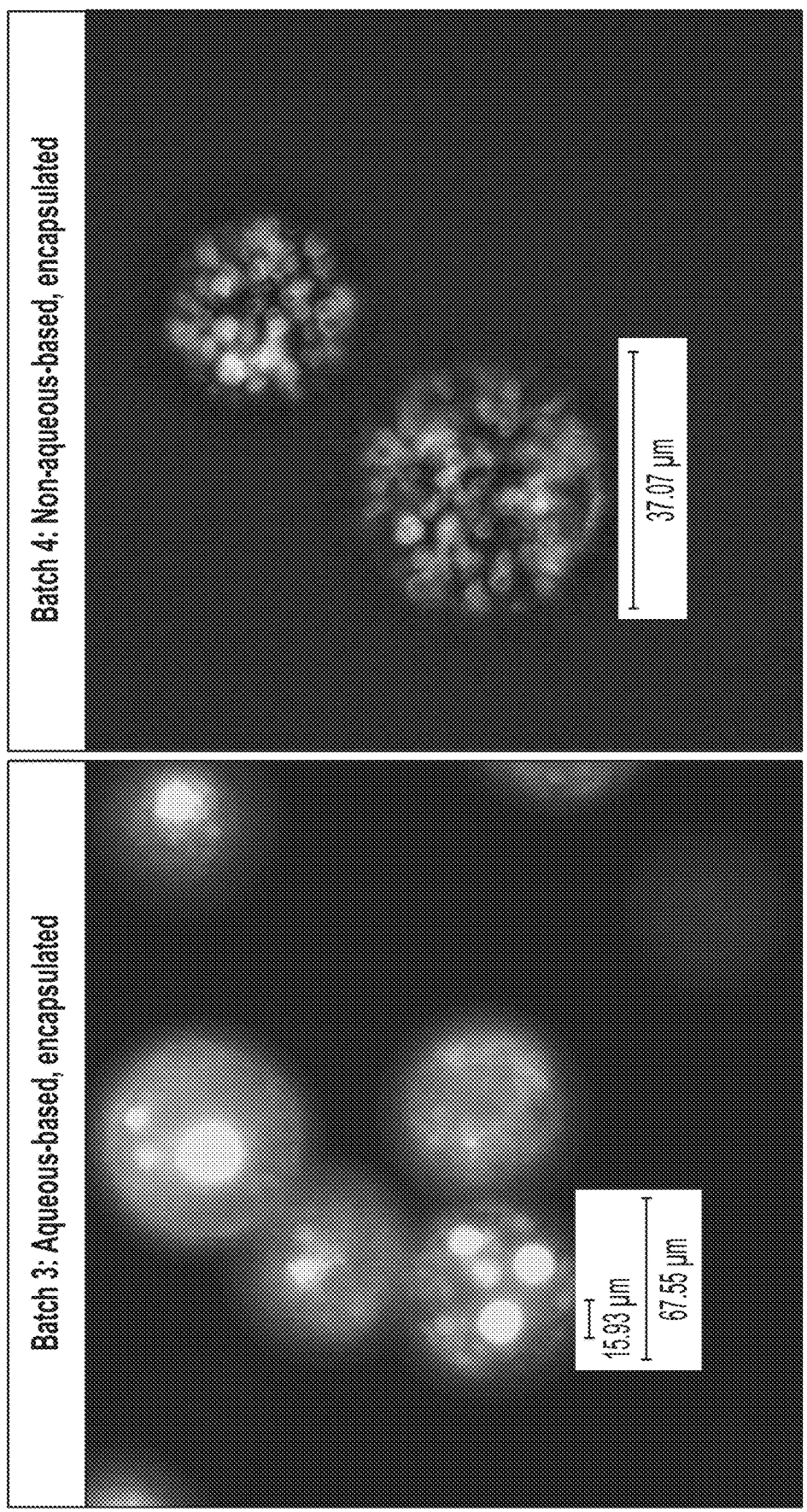
FIG. 20 contains fluorescence microscopy images of protein-encapsulated microspheres produced using aqueous and non-aqueous emulsion methods and show that SDPs are reconstituted and merged into bigger droplets using the aqueous emulsion method while retained their original raisin-shape using the non-aqueous emulsion method. Green fluorescent images are depicted in gray scale.

Fluorescent microscope images revealed the morphology and distribution of protein SDPs inside of the POE microspheres (FIG. 20). For Batch 3, SDPs were reconstituted by water during the encapsulation process and merged into larger droplets inside of the microsphere. To the contrary, for Batch 4, SDPs encapsulated inside of microspheres remained their original raisin-shaped structure indicating that the SDP remained its integrity after the process, as no reconstitution of protein by water.

The encapsulation efficiency (Measured protein loading in product/Theoretical protein loading) for Batch 3 and Batch 4 were determined to be 35.0% and 80.7% respectively (Table 12.). The more than double encapsulation efficiency for non-aqueous system suggests than SDP are better retained in the hydrocarbon droplets and less diffusion to the continues phase comparing to the aqueous system. The purity (percentage of monomer) of protein encapsulated in the POE microsphere was measured by size exclusion chromatography (SEC). The Batch 4 showed good retain of protein purity after the whole encapsulation process.

TABLE 12

Quantification and purity of protein encapsulated in POE microspheres.

| Samples | Emulsion system | Theoretical protein loading from feed solution* | Measured Protein loading in product | Encapsulation Efficiency | Bursted/ Total protein | VEGF Trap Purity by SEC* |
|---|---|---|---|---|---|---|
| Batch 3 | S/O/W | 6% | 2.10% | 35.0% | 0.7% | 96.4 |
| Batch 4 | S/H/F | 6% | 4.84% | 80.7% | 11.6% | 96.7 |

*original SDP contains 60% wt protein and 97.3% purity by SEC.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The present invention may be embodied in other specific forms without departing from the spirit or essential attributes thereof and, accordingly, reference should be made to the appended claims, rather than to the foregoing specification, as indicating the scope of the invention.

We claim:

1. A method of producing encapsulation efficient polymer-coated microparticles, wherein the method comprises:
   combining micronized protein powder and a polymer into a hydrocarbon solvent to form a non-aqueous first solution, wherein the micronized protein powder comprises at least one selected from the group consisting of an antibody and an Fc-fusion protein;

agitating the first non-aqueous solution to form a suspension;

feeding the suspension to a dispersion cell, wherein the suspension is infused through a porous membrane into a continuous phase comprising a fluorocarbon liquid and a fluorosurfactant under a tangent flow of the continuous phase to form a hydrocarbon-in-fluorocarbon emulsion;

adding a hydrofluoroether to the hydrocarbon-in-fluorocarbon emulsion;

removing the hydrocarbon solvent to provide hardened microparticles; and removing the fluorocarbon liquid to isolate the microparticles, wherein the microparticles comprise protein encapsulated within a matrix of polymer, wherein the protein is encapsulated at an efficiency of about 80% measured by protein loading in the polymer-coated microparticles or the theoretical protein loading from the first non-aqueous solution.

2. The method of claim 1, further comprising the steps of removing residual fluorosurfactant from the microparticles by washing the microparticles in the fluorocarbon liquid and removing the fluorocarbon by vacuum and collecting the microparticles using a polyethersulfone membrane filter.

3. The method of claim 1 wherein the fluorocarbon liquid comprises a perfluoro $C_5$-$C_{18}$ compound.

4. The method of claim 1, wherein the hydrocarbon solvent is selected from the group consisting of dichloromethane, chloroform, toluene, ethyl acetate, tetrahydrofuran, or a combination thereof.

5. The method of claim 1, wherein the fluorocarbon solution comprises 1,1,2,2,3,3,4,4,4-nonafluoro-N,N-bis (1,1,2,2,3,3,4,4,4-nonafluorobutyl) butan-1-amine.

6. The method of claim 1, wherein the fluorosurfactant comprises Perfluoropolyether-b-Polyethylene glycol-b-Perfluoropolyether.

7. The method of claim 1, wherein the polymer comprises polyorthoester (POE).

8. The method of claim 1, wherein the polymer is selected from the group consisting of polylactic acid and poly (lactic-co-glycolic acid).

9. The method of claim 1, wherein the hydrofluoroether is 2-(trifluoromethyl)-3-ethoxydodecafluorohexane.

10. The method of claim 1, wherein the porous membrane is a fluorophilic-coated stainless steel membrane.

11. The method of claim 10, wherein the pores of the porous membrane are 3 to 300 μm in diameter.

12. The method of claim 1, wherein the fluorosurfactant is present in fluorocarbon liquid at about 0.1 to 5% w/v.

13. The method of claim 1, wherein the protein powder to polymer ratio is 0.1%-30%.

14. The method of claim 1, wherein the Fc-fusion protein is a vascular endothelial growth factor (VEGF) Trap fusion protein.

15. The method of claim 14, wherein the VEGF-trap fusion protein is aflibercept.

16. A method of producing encapsulation efficient polymer-coated microparticles, wherein the method comprises:

combining a polymer and 1 to 30% w/w of total solid spray dried-protein suspended in a hydrocarbon solution to form a non-aqueous first solution, wherein the protein is selected from the group consisting of an antibody and an Fc-fusion protein;

agitating the first non-aqueous solution to form a suspension;

feeding the suspension to a dispersion pump, wherein the suspension is infused through a porous membrane into a continuous phase comprising a fluorocarbon liquid and 0.1 to 5.0% w/v fluorosurfactant under a tangent flow of the continuous phase to form a hydrocarbon-in-fluorocarbon emulsion;

removing the hydrocarbon solvent to provide hardened polymer-coated microparticles;

and removing the fluorocarbon liquid to isolate the microparticles, wherein the polymer-coated microparticles comprise protein encapsulated within a matrix of polymer, wherein the protein is encapsulated at an efficiency of about 80% measured by protein loading in the polymer-coated microparticles or the theoretical protein loading from the first non-aqueous solution.

17. The method of claim 16, further comprising the step of adding a hydrofluoroether into the fluorocarbon liquid of the hydrocarbon-in-fluorocarbon emulsion prior to removing the hydrocarbon solvent.

18. The method of claim 16, wherein the protein is aflibercept.

19. The method of claim 1, where the protein is encapsulated at an efficiency of 80.7% measured by protein loading in the polymer-coated microparticles or the theoretical protein loading from the first non-aqueous solution.

20. The method of claim 16, where the protein is encapsulated at an efficiency of 80.7% measured by protein loading in the polymer-coated microparticles or the theoretical protein loading from the first non-aqueous solution.

* * * * *